United States Patent
Lai et al.

(10) Patent No.: US 10,722,489 B2
(45) Date of Patent: Jul. 28, 2020

(54) D-3-PHOSPHOGLYCERATE DEHYDROGENASE ALLOSTERIC INHIBITOR AND USE THEREOF

(71) Applicant: Peking University, Beijing (CN)

(72) Inventors: Luhua Lai, Beijing (CN); Ying Liu, Beijing (CN); Qian Wang, Beijing (CN); Pei Liu, Beijing (CN)

(73) Assignee: Peking University, Shenzhen (CN)

( * ) Notice: Subject to any disclaimer, the term of this patent is extended or adjusted under 35 U.S.C. 154(b) by 0 days.

(21) Appl. No.: 16/405,569

(22) Filed: May 7, 2019

(65) Prior Publication Data

US 2019/0262303 A1     Aug. 29, 2019

Related U.S. Application Data

(62) Division of application No. 16/344,799, filed as application No. PCT/CN2016/113476 on Dec. 30, 2016.

(30) Foreign Application Priority Data

Oct. 31, 2016  (CN) .......................... 2016 1 0926351
Oct. 31, 2016  (CN) .......................... 2016 1 0941898

(51) Int. Cl.
  *A61K 31/15*   (2006.01)
  *A61K 31/341*  (2006.01)
  *A61P 35/00*   (2006.01)

(52) U.S. Cl.
  CPC ............ *A61K 31/341* (2013.01); *A61K 31/15* (2013.01); *A61P 35/00* (2018.01)

(58) Field of Classification Search
  CPC ................................................... A61K 31/15
  See application file for complete search history.

(56) References Cited

U.S. PATENT DOCUMENTS

| | | | | |
|---|---|---|---|---|
| 2005/0069555 | A1* | 3/2005 | Barsanti | A61K 31/175 424/184.1 |
| 2010/0035932 | A1 | 2/2010 | Schepetkin | |
| 2011/0251182 | A1* | 10/2011 | Sun | A61K 31/427 514/218 |
| 2016/0024038 | A1* | 1/2016 | Stutzmann | C07D 307/54 514/254.1 |

FOREIGN PATENT DOCUMENTS

WO     2011069039     9/2011

OTHER PUBLICATIONS

Lidia, et al. Document No. 160:294964, retrieved from STN; Feb. 6, 2014.*
Cancer and Metastasis Reviews (1998), 17(1), 91-106.*
Science (1999), vol. 286, 531-537.*
Cancer [online], [retrieved on Jul. 6, 2007]. Retrieved from the internet, URL http://www.nlm.nih.gov/medlineplus/cancer.html>.*
Ferreira de Melo, et al. Document No. 164:296241, retrieved from STN; 2014.*
Li, et al. Document No. 160:702782, retrieved from STN; 2014.*
Cardozo, et al. Document No. 158:645368, retrieved from STN; May 2, 2013.*
Cachiba, et al. Document No. 158:243438, retrieved from STN; 2012.*
Kuemmerle, et al. Document No. 151:381322, retrieved from STN; 2009.*
Skretas, et al. Document No. 147:226113, retrieved from STN; 2007.*
Novacek, et al. Document No. 84:105494, retrieved from STN; 1975.*
"Nature" vol. 476, p. 346-350, "Functional genomics reveal that the serine synthesis pathway is essential in breast cancer" by Possemato, Jul. 14, 2011.
"Nature Genetics" vol. 43, 9, p. 869-874, "Phosphoglycerate dehydrogenase diverts glycolytic flux and contributes to oncogenesis", by Locasale, Jul. 31, 2011.
International Journal Pharmaceutical Sciences and Research, vol. 6 4, p. 1792-1804, "Synthesis and evaluation of novel thiosemicarbazone derivatives as anticancer agents", by Gokhale, Apr. 1, 2015.

* cited by examiner

*Primary Examiner* — Shawquia Jackson
(74) *Attorney, Agent, or Firm* — SV Patent Service

(57) ABSTRACT

This application discloses a D-3-phosphoglycerate dehydrogenase allosteric inhibitor and the use thereof. In one class is the benzoyl hydrazine compound for the allosteric site MDL-1 of the enzyme, and the other class is the furan compound for the allosteric site MDL-2 of the enzyme. In vitro enzymatic activity tests, cell viability tests and mouse xenograft model experiments confirm that the two classes of allosteric inhibitors can specifically inhibit the activity of D-3-phosphoglycerate dehydrogenase and delay the growth of cancer cells by reducing the overexpression of the enzyme in cancer cells. Same are used alone or in combination, or in combination with other anti-cancer drugs and can treat, prevent, or inhibit tumor diseases, including breast cancer, colon cancer, melanoma and non-small cell lung cancer.

8 Claims, 2 Drawing Sheets

D-3-PHOSPHOGLYCERATE DEHYDROGENASE ALLOSTERIC INHIBITOR AND USE THEREOF

FIELD OF THE INVENTION

The present invention relates to a drug for treatment and prevention of various diseases caused by metabolic disorder of serine, and specifically, to N'-substituted benzoyl hydrazide compounds as D-3-phosphoglycerate dehydrogenase inhibitors, and the application of the compounds and their combinations in the treatment of diseases, such as breast cancer, colon cancer, melanoma and non-small cell lung cancer.

BACKGROUND OF THE INVENTION

D-3-phosphoglycerate dehydrogenase (PHGDH) in humans catalyzes the first step of serine biosynthesis and is a key enzyme in the serine synthesis pathway. PHGDH was shown to be overexpressed in 40% of melanoma and 70% of triple negative breast cancer cells in 2011. Knockout experiments with the PHGDH gene revealed that the growth of these cancer cells was greatly inhibited [(1) Locasale, J. W., et al. (2011). Nat. Genet. 43, 869-874. (2) Possemato, R., et al. (2011). Nature 476, 346-350.]. Therefore, using PHGDH as an anti-cancer target for drug design has a broad prospect. Because the active pocket of PHGDH is small, the physiological concentration of the cofactor $NAD^+$ is as high as 0.3 mM, and the complete crystal structure of PHGDH has not been solved yet, drug design based on PHGDH active pocket goes slowly. The new strategy is to carry out allosteric regulation of PHGDH and design allosteric inhibitors of PHGDH.

Allosteric regulation in proteins refers to the phenomenon that allosteric effectors bind to the inactive sites of the protein and cause changes of the protein activity. Allosteric drugs showed better properties by increasing selectivity, regulating the activity of the target protein without complete loss of protein activity, only exhibiting allosteric ability in the presence of endogenous ligand, etc.

Recent studies have identified PHGDH gene knockdown combined with cisplatin or doxorubicin can significantly increase the biological activity of these anti-cancer drugs in vitro and in vivo [(3) Jing, Z., et al. (2015). Cancer Biol. Ther. 16, 541-548. (4) Zhang, X., and Bai, W., (2016). Cancer Chemother. Pharmacol. 78, 655-659.]. The studies provide reference for cancer therapy using the combination of PHGDH inhibitors and anti-cancer drugs. Till now, there is no report for PHGDH inhibitors in clinical research or the drug effects of PHGDH inhibitors combined with other anti-cancer drugs. Carrying out drug design targeting allosteric sites of PHGDH and using allosteric inhibitors for tumor prevention and treatment is novel and creative.

SUMMARY OF THE INVENTION

The aim of the present invention is providing compounds which are allosteric inhibitors of PHGDH, to treat and prevent certain diseases such as breast cancer, colon cancer, melanoma and non-small cell lung cancer.

The aim of the present invention is also providing the compounds in combination with other PHGDH inhibitors or anticancer drugs, to treat and prevent certain diseases such as breast cancer, colon cancer, melanoma and non-small cell lung cancer.

The present invention identified two potential allosteric sites, MDL-1 and MDL-2 (FIG. 1), by analyzing the surface properties of PHGDH protein and performing virtual screening at the two sites.

In a first general aspect, the present invention provides benzoylhydrazine compounds at allosteric site MDL-1 as allosteric inhibitors of PHGDH, which share a common structural formula (I):

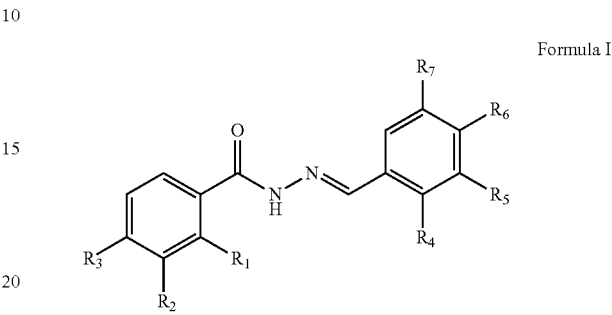

Formula I

In Formula 1, $R_1$, $R_2$, $R_3$, $R_4$, $R_5$, $R_6$ and $R_7$ can be identical or different; each independently represents hydrogen, halo, nitro, hydroxyl, amino or substituted amino, alkyl, alkoxy, benzyloxy and haloalkyl; or the two adjacent substituents ($R_1$ and $R_2$, $R_2$ and $R_3$, $R_4$ and $R_5$, $R_5$ and $R_6$, $R_6$ and $R_7$) can form a ring.

The halo includes F, Cl, Br, and I.

The substituted amino is preferably C1~C12 alkyl group substituted amino, more preferably C1~C6 alkyl substituted amino, such as methylamine, ethylamine, dimethylamino, diethylamino, etc. The alkyl group is preferably C1~C12 alkyl group, more preferably C1~C6 alkyl group, such as methyl, ethyl, propyl, isopropyl, butyl, etc.

The alkoxy group is preferably C1~C8 alkoxy, more preferably C1~C4 alkoxy, such as methoxyl, ethoxy, propoxy, etc. The halo substituted alkyl group is preferably C1~C12 alkyl substituted by one or more halo, more preferably C1~C6 alkyl substituted by one or more halo, such as trifluoromethyl.

In Formula 1, when they ($R_1$ and $R_2$, $R_2$ and $R_3$, $R_4$ and $R_5$, $R_5$ and $R_6$ and/or $R_6$ and $R_7$) are linked into ring, the two adjacent substituents represent buta-1, 3-diene-1,4-diyl and buta-2-ene-1,4-dily with a benzene ring fused to form naphthalene, trahydronaphthalene, etc.

The compound of formula I can be prepared by the following method:

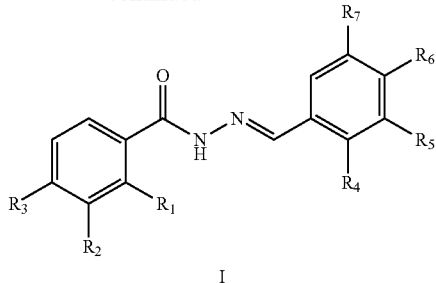

I

The corresponding compounds of Formula I were prepared by a condensation reaction between the substituted benzoyl hydrazide and a substituted benzaldehyde. Specific embodiments can be found in Implementation Example 2.

In a second general aspect, the present invention provides furan compounds at allosteric site MDL-2 as allosteric inhibitors of PHGDH, which share a common structural formula (II):

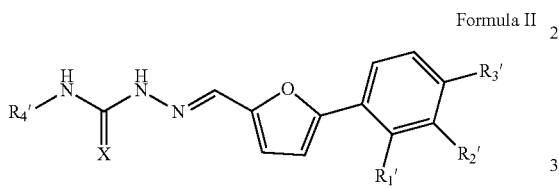

Formula II

In Formula II, $R_1'$, $R_2'$ and $R_3'$ are identical or different; each independently represents hydrogen, halo, nitro, hydroxyl, amino, carboxyl, alkyl, alkoxy, haloalkyl, carboxylic ester, sulfonamide, amide or N-alkyl substituted amide; or wherein two adjacent substituents (R1' and R2' or R2' and R3') can form a ring; $R_4'$ independently represents alkyl, haloalkyl, amino, cycloalkyl, unsubstituted or substituted aryl; and X is oxygen, nitrogen or sulfur.

The halo includes F, Cl, Br, and I.

When one or more of $R_1'$, $R_2'$ and $R_3'$ are alkyl groups, the C1~C12 alkyl group is preferred, more preferably C1~C6 alkyl group, such as methyl, ethyl, isopropyl, etc.; when they are alkoxy group, the C1~C8 alkoxy is preferred, more preferably C1~C4 alkoxy, such as methoxyl group, ethoxy group, propoxy group, etc.; when they are haloalkyl group, the C1~C12 alkyl group substituted by one or more halo is preferred, more preferably C1~C6 alkyl substituted by one or more halo, mostly fluorine substituted compound, such as trifluoromethyl.

When one or more of $R_1'$, $R_2'$ and $R_3'$ are the carboxylic ester group, the C1~C8 ester group is preferred (—COOC$_n$H$_{2n+1}$, n=integer from 1 to 7), more preferably C1~C4 ester, such as methoxyl ester, ethoxy ester, isopropyl ester, etc.

When one or more of $R_1'$, $R_2'$ and $R_3'$ are N-alkyl substituted amide groups, the C1~C12 alkyl substituted amide group is preferred, more preferably C1~C6 alkyl substituted amide group, such as N-methyl amide group, N, N-dimethyl amide group, etc.

When $R_1'$ and $R_2'$ or $R_2'$ and $R_3'$ are linked into ring, the two adjacent substituents represent buta-1,3-diene-1,4-diyl, buta-2-ene-1,4-dily, etc.

When $R_4'$ is alkyl group, the C1~C12 alkyl group is preferred, more preferably C1~C6 alkyl, such as methyl, ethyl, isopropyl, etc.

When $R_4'$ is haloalkyl group, the C1~C12 alkyl group substituted by one or more halo is preferred, more preferably C1~C6 alkyl substituted by one or more halo, such as trifluoromethyl.

When $R_4'$ is cycloalkyl group, the C5~C7 cycloalkyl group is preferred, such as cyclohexyl.

When $R_4'$ is unsubstituted or substituted aryl, the aryl is preferably phenyl, the substituted aryl is preferably 4-substituted phenyl, and the substituted group on phenyl is preferably C1~C6 alkyl, C1~C6 alkyl group substituted by one or more halo, nitro, C1~C4 alkoxy, etc., such as 4-trifluoromethyl phenyl, 4-nitro phenyl, etc.

The compound of Formula II can be prepared by the following method:

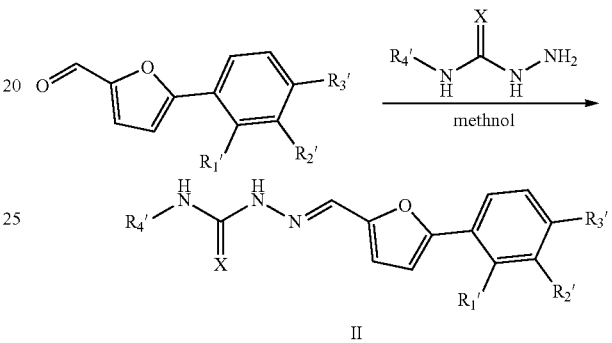

II

The corresponding inhibitors of Formula II were prepared by a condensation reaction between the substituted furan aldehyde and substituted semicarbazide (or a substituted thiosemicarbazide or a substituted aminooxime).

Specific examples of compounds of Formula 11 can be found in Implementation Example 3.

The chemical substances used in the synthetic route of the present invention are marketable products or can be synthesized by the existing technology. The operation methods and steps, and reaction conditions and intermediates are designed and implemented according to the organic synthesis method well known to the technical personnel in the field, which are disclosed in the implementation examples.

The present invention proves that compounds of Formula I and II can selectively inhibit PHGDH through enzymatic activity assays, cell-based assays and mouse tumor model. The compounds of Formula I and II can allosterically inhibit PHGDH activity, reduce the overexpression of PHGDH in cancer cells and suppress the growth of cancer cells.

By using the benzoylhydrazine compounds or furan compounds in the present invention alone, together or combined with other PHGDH inhibitors or anti-cancer drugs, using their pharmaceutical salts as active ingredients, or adding conventional drug carriers, drugs for treatment or prevention of various cancers can be prepared.

Pharmaceutical salts of benzoylhydrazine compounds or furan compounds and all combinations in the present invention refer to pharmaceutically acceptable salts, including those formed with inorganic acids such as hydrochloric acid, sulfuric acid, phosphoric acid and nitric acid, and those formed with organic acids such as citric acid, succinic acid, citric acid, acetic acid, tartaric acid and methyl sulfonic acid.

Conventional drug carriers refer to non-toxic solid, semi-solid or liquid fillers, diluents, adjuvants, wrapping materials or other pharmaceutical excipients. According to the well-known technology in the field, the pharmaceutical compositions can be formulated into a variety of dosage forms according to the needs of therapeutic purposes and delivery routes.

DETAILED DESCRIPTION OF THE INVENTION

Herein below, implementation examples of the present invention will be described. The following implementation examples are provided only to illustrate the present invention, and they are not intended to limit the present invention only to these implementation examples. Those skilled people will find other methods for carrying out the invention that are obvious to them, and those methods are considered to be included in the scope of the present invention.

Implementation Example 1. Discovery of Allosteric Inhibitors of PHGDH

1) Prediction of Allosteric Sites of PHGDH

Figure 1:
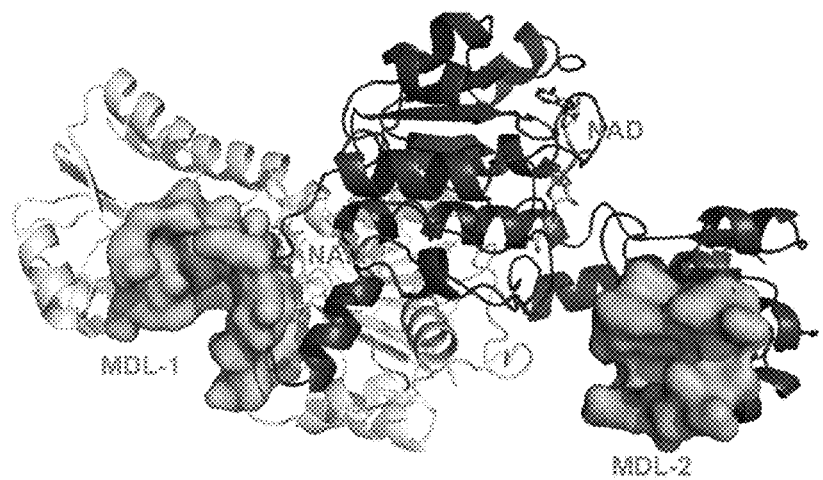
FIG. 1 shows the allosteric site of PHGDH predicted by the protein surface property detection program CAVITY.

Potential allosteric sites in PHGDH (PDB code: 2G76) were predicted by the protein surface detection program CAVITY. Firstly, the program used a fictitious ball rolling around the surface of a protein to detect the inaccessible site. Secondly, the ability of the protein to bind small molecules based on the empirical formula (CavityScore=(Volume−AdjustVolume)/(SurfaceArea−AdjustSurfaceArea)) was scored. AdjustVolume and AdjustSurfaceArea are related to the surface area of the hydrophobic residues and the number of hydrogen bond acceptors and donors at the predicted sites. A good linear relationship was obtained by scoring the maximum $pK_D$ of the known binding site-ligand binding pair and fitting it to known experimental $pK_D$ values. Based on the value of $pK_D$ and the pocket volume, the appropriate potential allosteric sites are finally selected. We are the first to predict two novel allosteric sites in PHGDH, MDL-1 and MDL-2. From FIG. 1, MDL-1 is close to the active site and the NAD+/NADH-cofactor binding site, with a volume of 847.4 $Å^3$ and a predicted maximal $pK_D$ of 8.71. It shares residues Gly 78, Val 79, Asp 80, Asn 81 and Val 82 with the active site. MDL-2 is located in the substrate binding domain, with a pocket volume of 463.4 $Å^3$ and a predicted maximal $pK_D$ of 7.79.

2) Virtual Screening of Allosteric Molecules of PHGDH

For the predicted allosteric sites, the molecular docking method is used to perform virtual screening of the SPECS database. After manually selected, purchased compounds were verified in in vitro enzyme activity assays.

(E)-2,4-dihydroxy-N'-(2-hydroxy-5-nitrobenzylidene) benzohydrazide in MDL-1 was confirmed to have the half maximal inhibitory concentration ($IC_{50}$) less than 50 μM and named PKUMDL-WL-2101. The binding mode of PKUMDL-WL-2101 in MDL-1 was shown in FIG. 2A.

(Z)-2-chloro-4-(5-((2-(ethylcarbamothioyl) hydrazono) methyl) furan-2-yl) benzoic acid in MDL-2 was also confirmed to have the $IC_{50}$ value less than 50 μM and named PKUMDL-WL-2201. The binding mode of PKUMDL-WL-2201 in MDL-2 was shown in FIG. 2B.

Implementation Example 2. The Synthesis of Allosteric Molecules at Site MDL-1

1) The Design of PKUMDL-WL-2101 Analogues

Figure 2:
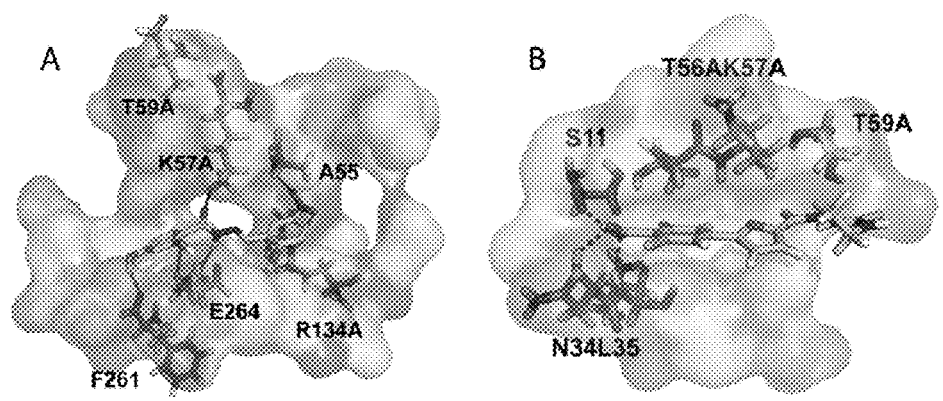
FIG. 2 depicts the binding mode of molecules of compounds in the present invention and PHGDH. A: PKUMDL-WL-2101 in MDL-1; B: PKUMDL-WL-2201 in MDL-2.

The analysis is shown in FIG. 2A. The interactive model of small molecules with PHGDH can be seen: Two benzene rings occupied the hydrophobic cavity in the pocket. On the acyl benzene ring, 4-hydroxyl can form hydrogen bond with Phe 261, 2-hydroxyl can form hydrogen bond with Glu 264, carbonyl oxygen of hydrazide chain can form hydrogen bond with Lys 57, and nitrogen of hydrazine can form hydrogen bond with Glu 264; on the other benzene ring, 3-nitro can form hydrogen bond with Arg 134 or Ala 55; and meanwhile the ring has electrostatic effect with the surrounding positively charged cavity. According to these, two benzene ring substituted groups were optimized and a series of PKUMDL-WL-2101 analogues have been designed.

2) The Synthesis of PKUMDL-WL-2101 and its Analogues

Using PKUMDL-WL-2101 as an example, the synthesis of PHGDH inhibitors of benzoylhydrazine is described. The synthetic route is as follows.

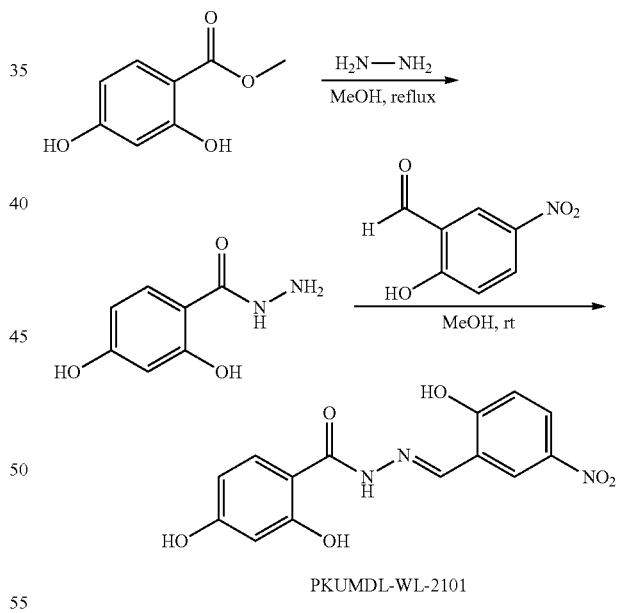

PKUMDL-WL-2101

Experimental procedures are as follow.

(1) To a solution of methyl 2,4-dihydroxybenzoate (1.781 g, 11.5 mmol) in methanol (50 mL), 85% hydrazine hydrate (2.031 g, 34.5 mmol) was added. The mixture was stirred and refluxed. After the reaction was completed (monitored by TLC), the solvent was eliminated in vacuo, and the resulting residue was cooled and recrystallized in methanol to obtain 2,4-dihydroxybenzohydrazide as a white solid (1.546 g, 80%). $^1$H-NMR (400 MHz, DMSO): 6.35 (2H, m), 7.77 (1H, d, J=9.20 Hz), 10.06 (1H, s), 10.69 (1H, s), 11.86 (1H, s).

(2) A mixture containing 2,4-dihydroxybenzohydrazide (1.681 g, 10.0 mmol) and 2-hydroxy-5-nitrobenzaldehyde (1.670 g, 10.0 mmol) in methanol (50 mL) was stirred at room temperature. After the reaction was completed (monitored by TLC), the solvent was eliminated in vacuo, and the resulting residue was recrystallized in methanol to obtain (E)-2,4-dihydroxy-N'-(2-hydroxy-5-nitrobenzylidene) benzohydrazideas an orange solid (2.378 g, 75%). Mp: 296-298° C. $^1$H-NMR (DMSO): 6.33 (1H, d, J=1.80 Hz), 6.39 (1H, dd, J=1.98, 8.92 Hz), 7.12 (1H, d, J=8.99 Hz), 7.81 (1H, d, J=8.75 Hz), 8.18 (1H, dd, J=2.64, 9.20 Hz), 8.57 (1H, d, J=2.57 Hz), 8.73 (1H, s), 10.26 (1H, s), 12.02 (1H, s), 12.15 (1H, s), 12.32 (1H, s); $^{13}$C NMR (101 MHz, DMSO-d6) δ 165.32, 162.95, 162.55, 162.19, 144.51, 139.85, 129.84, 126.47, 123.83, 119.78, 117.06, 107.58, 105.83, 102.81. HRMS (ESI-MS): measured value (theoretical value [(M+H)+]) (318.1)318.1.

The other thirty-one benzoyl hydrazine compounds were prepared by using the above method and the data characterizing the novel compounds was shown in Table 1. $^1$H and $^{13}$C NMR spectra were recorded on a USA Varian Mercury 400 MHz spectrometer. The chemical shiftvalues (δ) are reported in ppm relative to tetramethylsilane as internal standard in DMSO-d6. The coupling constant is expressed in Hz. The abbreviation used is: s=singlet, d=doublet, t=triplet, q=quartet, m=multiplet and br=broad. Melting points were determined on an X-4 microscopic melting point apparatus made by Beijing Tech Instrument Co., Ltd.

TABLE 1

Characterization of novel benzoyl hydrazine compounds

| Number | Structure | Mp (° C.) | $^1$H NMR(δ) |
|---|---|---|---|
| PKUMDL-WL-2113 | (2,4-dihydroxybenzohydrazide linked via N'=CH to 4-ethoxy-3-nitrophenyl) | 239-241 | 12.27 (s, 1H), 11.77 (s, 1H), 10.24 (s, 1H), 8.42 (s, 1H), 8.20 (d, J = 2.2 Hz, 1H), 8.00 (dd, J = 8.8, 2.2 Hz, 1H), 7.80 (d, J = 8.8 Hz, 1H), 7.46 (d, J = 8.9 Hz, 1H), 6.41-6.29 (m, 2H), 4.28 (q, J = 6.9 Hz, 2H), 3.33 (s, 33H), 1.36 (t, J = 6.9 Hz, 3H). |
| PKUMDL-WL-2116 | (2,4-dihydroxybenzohydrazide linked via N'=CH to 4-methoxy-3-nitrophenyl) | 265-267 | 12.27 (s, 1H), 11.77 (s, 1H), 10.24 (s, 1H), 8.43 (s, 1H), 8.22 (d, J = 2.1 Hz, 1H), 8.03 (dd, J = 8.9, 2.1 Hz, 1H), 7.80 (d, J = 8.8 Hz, 1H), 7.48 (d, J = 8.9 Hz, 1H), 6.41-6.29 (m, 2H), 3.99 (s, 3H). |
| PKUMDL-WL-2128 | (4-trifluoromethylbenzohydrazide linked via N'=CH to 2-hydroxy-5-nitrophenyl) | >300 | 12.43 (s, 1H), 12.25 (s, 1H), 8.77 (s, 1H), 8.63 (d, J = 2.9 Hz, 1H), 8.24-8.12 (m, 3H), 7.95 (d, J = 8.2 Hz, 2H), 7.13 (d, J = 9.1 Hz, 1H). |
| PKUMDL-WL-2129 | (2,4-dihydroxybenzohydrazide linked via N'=CH to 4-fluorophenyl) | 224-226 | 12.32 (s, 1H), 11.70 (s, 1H), 10.23 (s, 1H), 8.44 (s, 1H), 7.84-7.75 (m, 3H), 7.31 (t, J = 8.9 Hz, 2H), 6.41-6.29 (m, 2H). |
| PKUMDL-WL-2132 | (2,4-dihydroxybenzohydrazide linked via N'=CH to 2-nitrophenyl) | 256-258 | 12.27 (s, 1H), 12.02 (s, 1H), 10.29 (s, 1H), 8.84 (s, 1H), 8.15-8.05 (m, 2H), 7.83 (dd, J = 8.2, 5.8 Hz, 2H), 7.74-7.65 (m, 1H), 6.38 (dd, J = 8.7, 2.4 Hz, 1H), 6.32 (d, J = 2.4 Hz, 1H). |

The corresponding names of the compounds are:

1) PKUMDLWL-2101: (E)-2,4-dihydroxy-N'-(2-hydroxy-5-nitrobenzylidene)benzohydrazide;

2) PKUMDLWL-2102: (E)-N'-(4-fluorobenzylidene)benzohydrazide;

3) PKUMDLWL-2103: (E)-N'-benzylidene-2,4-dihydroxybenzohy drazide;

4) PKUMDLWL-2104: (E)-2,4-dihydroxy-N'-(naphthalen-1-ylmethylene)benzohydrazide;

4) PKUMDLWL-2105: (E)-2,4-dihydroxy-N'-(4-nitrobenzylidene)benzohydrazide;

6) PKUMDLWL-2106: (E)-N'-(2-hydroxy-5-nitrobenzylidene)-4-nitrobenzohydrazide;

7) PKUMDLWL-2107: (E)-N'-(2-hydroxy-5-nitrobenzylidene)-1-naphthohydrazide;
8) PKUMDLWL-2108: (E)-N'-(2-hydroxy-5-nitrobenzylidene)-4-methylbenzohydrazide;
9) PKUMDLWL-2109: (E)-2,4-dihydroxy-N'-(4-hydroxybenzylidene)benzohydrazide;
10) PKUMDLWL-2110: (E)-2-hydroxy-N'-(2-hydroxy-5-nitrobenzylidene)benzohydrazide;
11) PKUMDLWL-2111: (E)-4-fluoro-N'-(2-hydroxy-5-nitrobenzylidene)benzohydrazide;
12) PKUMDLWL-2112: (E)-2,4-dihydroxy-N'-(3-methylbenzylidene)benzohydrazide;
13) PKUMDLWL-2113: (E)-N'-(4-ethoxy-3-nitrobenzylidene)-2,4-dihydroxybenzohvdrazide;
14) PKUMDLWL-2114: (E)-2,4-dihydroxy-N'-(3-nitrobenzylidene)benzohydrazide;
15) PKUMDLWL-2115: (E)-3-hydroxy-N'-(2-hydroxy-5-nitrobenzylidene)benzohydrazide;
16) PKUMDLWL-2116: (E)-2,4-dihydroxy-N'-(4-methoxy-3-nitrobenzylidene)benzohydrazide;
17) PKUMDLWL-2117: (E)-2,4-dihydroxy-N'-(3-hydroxyvbenzylidene)benzohydrazide;
18) PKUMDLWL-2118: (E)-4-hydroxy-N'-(2-hydroxy-5-nitrobenzylidene)benzohydrazide;
19) PKUMDLWL-2119: (E)-3-chloro-N'-(2-hydroxy-5-nitrobenzylidene)benzohydrazide;
20) PKUMDLWL-2120: (E)-N'-(2-hydroxy-5-nitrobenzylidene)-3-nitrobenzohydrazide;
21) PKUMDLWL-2121: (E)-4-amino-N'-(2-hydroxy-5-nitrobenzylidene)benzohydrazide;
22) PKUMDLWL-2122: (E)-N'-(2-hydroxy-5-nitrobenzylidene)-2-methylbenzohydrazide;
23) PKUMDLWL-2123: (E)-4-ethoxy-N'-(2-hydroxy-5-nitrobenzylidene)benzohydrazide
24) PKUMDLWL-2124: (E)-4-(tert-butyl)-N'-(2-hydroxy-5-nitrobenzylidene)benzohydrazide;
25) PKUMDLWL-2125: (E)-4-bromo-N'-(2-hydroxy-5-nitrobenzylidene)benzohydrazide
26) PKUMDLWL-2126: (E)-N'-(2-hydroxy-5-nitrobenzylidene)-3-methylbenzohydrazide
27) PKUMDLWL-2127: (E)-4-chloro-N'-(2-hydroxy-5-nitrobenzylidene)benzohydrazide
28) PKUMDLWL-2128: (E)-N'-(2-hydroxy-5-nitrobenzylidene)-4-(trifluoromethyl)benzohydrazide
29) PKUMDLWL-2129: (E)-N'-(4-fluorobenzylidene)-2,4-dihydroxybenzohydrazide;
30) PKUMDLWL-2130: (E)-N'-(4-chlorobenzylidene)-2,4-dihydroxybenzohydrazide
31) PKUMDLWL-2131: (E)-N'-(4-bromobenzylidene)-2,4-dihydroxybenzohydrazide
32) PKUMDLWL-2132: (E)-2,4-dihydroxy-N'-(2-nitrobenzylidene)benzohydrazide Implementation Example 3. The Synthesis of Allosteric Molecules at Site MDL-2

1) The Design of PKUMDL-WL-2201 Analogues

The interaction pattern of small molecules with PHGDH can be seen from FIG. 2B: 2-phenylfuran occupied the hydrophobic cavity in the pocket; oxygen atom at 4-carboxylbenzene ring can form hydrogen bond with Ser 11, Leu 35 or Asn34; and aminothiourea groups may interact with other negatively charged groups in PHGDH. A series of its bioisosteric analogues have been designed through isostere of molecules and other strategies.

2) The Synthesis of PKUMDL-WL-2201 and its Analogues

Using PKUMDL-WL-2201 as an example, the synthesis of furan molecules of PHGDH inhibitors is described. The synthetic route is as follows.

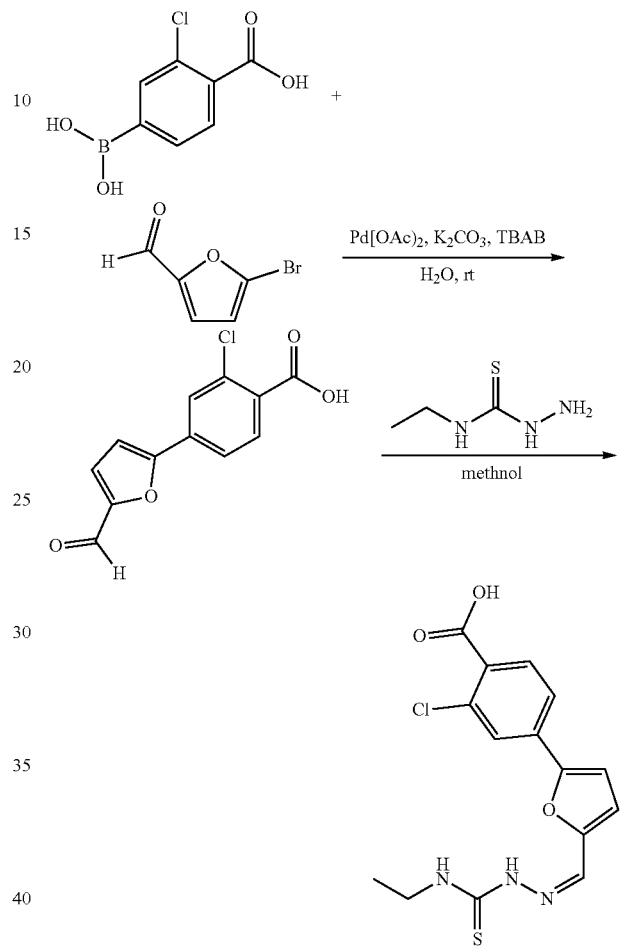

Experimental procedures are as follow.
(1) A mixture containing 4-borono-2-chlorobenzoic acid (1.342 g, 6.70 mmol), 5-bromofuran-2-carbaldehyde (1.406 g, 8.04 mmol), TBAB (2.160 g, 6.70 mmol), Pd (OAc)$_2$ (0.015 g, 0.07 mmol). K$_2$CO$_3$ (1.420 g, 13.4 mmol) and water (100 ml) in a 250 mL round bottom flask was stirred at room temperature under argon protection. After the reaction was completed (monitored by TLC), furan raw material points were eliminated. The mixture was extracted with EtOAc (50 mL×3). Then the water phase was acidified with 3N HCl, a lot of precipitation was collected by filtration and dried to obtain the target product 2-chloro-4-(5-formylfuran-2-yl) benzoic acid (1.055 g, yellow solid, 63%). $^1$H-NMR (400 MHz, DMSO): 7.55 (1H, d, J=3.76 Hz), 7.70 (1H, d, J=3.76 Hz), 7.92 (2H, m), 8.05 (1H, d, J=1.28 Hz), 9.67 (1H, s).
(2) 2-chloro-4-(5-formylfuran-2-yl) benzoic acid (0.100 g, 0.40 mmol) obtained in Step 2 and 4-ethyl-3-thiosemicarbazide (0.048 g, 0.40 mmol) in methanol (20 mL) was stirred at room temperature. After the reaction was completed (monitored by TLC), the solvent was eliminated in vacuum by reduced pressure distillation, and the residue was recrystallized in methanol to obtain the target product PKUMDL-WL-2201 (orange solid, 0.126 g, 90%). Mp:

271-273° C., $^1$H-NMR (DMSO): 1.18 (3H, t, J=7.08 Hz), 3.62 (2H, m, J=6.81 Hz), 7.13 (1H, d, J=3.65 Hz), 7.39 (1H, d, J=3.60 Hz), 7.87 (2H, q, J=9.09 Hz), 7.98 (1H, s), 8.01 (1H, s), 8.39 (1H, t, J=5.85 Hz), 11.54 (1H, s), 13.40 (1H, s); $^{13}$C NMR (101 MHz, DMSO-d6) δ 176.46, 166.09, 151.84, 150.43, 133.19, 132.89, 131.84, 131.18, 129.57, 125.36, 122.15, 115.10, 111.42, 38.32, 14.51. HRMS (ESI): 352.0 (352.0, theoretical value [(M+H)+].

The other thirty furan compounds were prepared by the above method. The corresponding names of the compounds are:

PKUMDL-WL-2202: (E)-N-ethyl-2-((5-(4-(trifluoromethyl) phenyl) furan-2-yl) methylene) hydrazinecarbothioamide.

PKUMDL-WL-2203: (E)-N-ethyl-2-((5-(4-methoxyphenyl) furan-2-yl) methylene) hydrazinecarbothioamide.

PKUMDL-WL-2204: (E)-2-((5-(3-chlorophenyl) furan-2-yl) methylene)-N-ethylhydrazinecarbothioamide.

PKUMDL-WL-2205: (E)-4-(5-((2-(phenylcarbamothioyl) hydrazono) methyl) furan-2-yl) benzoic acid.

PKUMDL-WL-2206: (E)-4-(5-((2-(methylcarbamothioyl) hydrazono) methyl) furan-2-yl) benzoic acid.

PKUMDL-WL-2207: (E)-N-ethyl-2-((5-phenylfuran-2-yl) methylene) hydrazinecarbothioamide.

PKUMDL-WL-2208: (E)-2-((5-(4-(tert-butyl) phenyl) furan-2-yl) methylene)-N-ethylhydrazinecarbothioamide.

PKUMDL-WL-2209: (E)-2-chloro-5-(5-((2-(ethylcarbamothioyl) hydrazono) methyl) furan-2-yl) benzoic acid.

PKUMDL-WL-2210: (E)-Methyl 4-(5-((2-(ethylcarbamoyl) hydrazono) methyl) furan-2-yl) benzoate.

PKUMDL-WL-2211: (E)-N-ethyl-2-((5-(p-tolyl) furan-2-yl) methylene) hydrazinecarbothioamide.

PKUMDL-WL-2212: (E)-Methyl 4-(5-((2-((4-nitrophenyl) carbamothioyl) hydrazono) methyl) furan-2-yl) benzoate.

PKUMDL-WL-2213: (E)-4-(5-((2-(cyclohexylcarbamothioyl) hydrazono) methyl) furan-2-yl) benzoic acid.

PKUMDL-WL-2214: (E)-N-ethyl-2-((5-(naphthalen-1-yl) furan-2-yl) methylene) hydrazinecarbothioamide.

PKUMDL-WL-2215: (E)-methyl 4-(5-((2-(2-(4-(trifluoromethyl) phenyl) Hydrazinecarbonothioyl) hydrazono) methyl) furan-2-yl) benzoate.

PKUMDL-WL-2216: (E)-N-ethyl-2-((5-(4-fluorophenyl) furan-2-yl) methylene) hydrazinecarbothioamide.

PKUMDL-WL-2217: (E)-Methyl 2-amino-4-(5-((2-(hydrazinecarbonothioyl) hydrazono) methyl) furan-2-yl) benzoate.

PKUMDL-WL-2218: (E)-2-((5-(4-bromophenyl) furan-2-yl) methylene)-N-ethylhydrazinecarbothioamide.

PKUMDL-WL-2219: (E)-Isopropyl 4-(5-((2-(hydrazinecarbonothioyl) hydrazono) methyl) furan-2-yl) benzoate.

PKUMDL-WL-2220: (E)-Methyl 4-(5-((2-(hydrazinecarbonothioyl) hydrazono) methyl) furan-2-yl) benzoate.

PKUMDL-WL-2221: (E)-2-((5-(4-chlorophenyl) furan-2-yl) methylene)-N-ethylhydrazinecarbothioamide.

PKUMDL-WL-2222: (E)-4-(5-((2-(hydrazinecarbonothioyl) hydrazono) methyl) furan-2-yl) benzoic acid.

PKUMDL-WL-2223: (E)-Methyl 4-(5-((2-(hydrazinecarbonothioyl) hydrazono) methyl) furan-2-yl)-3-methylbenzoate.

PKUMDL-WL-2224: (E)-Methyl 4-(5-((2-(ethylcarbamothioyl) hydrazono) methyl) furan-2-yl) benzoate.

PKUMDL-WL-2225: (E)-4-(5-((2-(hydrazinecarbonothioyl) hydrazono) methyl) furan-2-yl) benzenesulfonamide.

PKUMDL-WL-2226: (E)-4-(5-((2-(ethylcarbamothioyl) hydrazono) methyl) furan-2-yl) benzoic acid.

PKUMDL-WL-2227: (E)-Ethyl 4-(5-((2-(hydrazinecarbonothioyl) hydrazono) methyl) furan-2-yl) benzoate.

PKUMDL-WL-2228: (E)-N-ethyl-2-((5-(4-nitrophenyl) furan-2-yl) methylene) hydrazinecarbothioamide.

PKUMDL-WL-2229: (E)-N-ethyl-2-((5-(4-hydroxyphenyl) furan-2-yl) methylene) hydrazinecarbothioamide.

PKUMDL-WL-2230: (E)-4-(5-((2-(hydrazinecarbonothioyl) hydrazono) methyl) furan-2-yl)-N-methylbenzamide.

PKUMDL-WL-2231: (E)-4-(5-((2-((4-(trifluoromethyl) phenyl) carbamothioyl) hydrazono) methyl) furan-2-yl) benzoic acid.

The data characterizing of the novel compounds was shown in Table 2.

TABLE 2

Characterization of novel furan compounds

| Number | Structure | Mp (° C.) | $^1$H NMR (δ) |
|---|---|---|---|
| PKUMDL-WL-2202 | 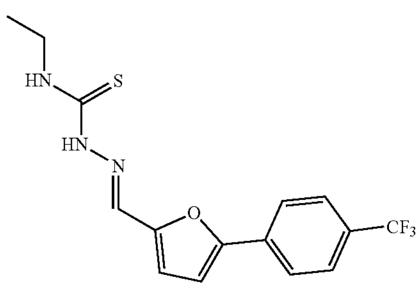 [SMILES: CCNC(=S)N/N=C/c1ccc(-c2ccc(C(F)(F)F)cc2)o1] | 184-186 | δ 11.57 (s, 2H), 9.16 (s, 2H), 8.38 (d, J = 6.1 Hz, 1H), 8.08-7.98 (m, 3H), 7.93 (s, 1H), 7.81 (d, J = 8.2 Hz, 2H), 7.36 (d, J = 3.7 Hz, 2H), 7.13 (d, J = 3.6 Hz, 2H), 3.66-3.57 (m, 2H), 1.17 (t, J = 7.1 Hz, 3H). |

TABLE 2-continued

Characterization of novel furan compounds

| Number | Structure | Mp (° C.) | ¹H NMR (δ) |
|---|---|---|---|
| PKUMDL-WL-2203 | 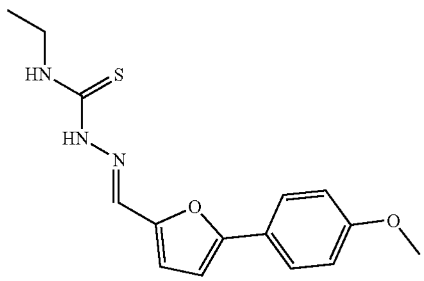 [SMILES: CCNC(=S)N/N=C/c1ccc(-c2ccc(OC)cc2)o1] | 168-170 | δ 11.44 (s, 1H), 8.29 (t, J = 5.9 Hz, 1H), 7.96 (s, 1H), 7.77 (d, J = 8.9 Hz, 1H), 7.02 (dd, J = 6.3, 2.6 Hz, 3H), 6.97 (d, J = 3.5 Hz, 1H), 3.81 (s, 3H), 3.60 (p, J = 7.0 Hz, 2H), 1.16 (t, J = 7.1 Hz, 3H). |
| PKUMDL-WL-2204 | 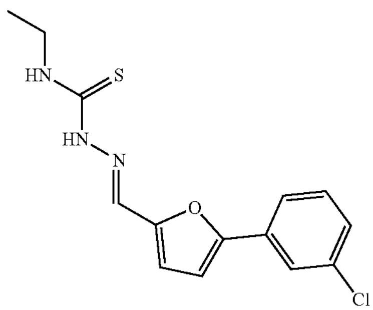 [SMILES: CCNC(=S)N/N=C/c1ccc(-c2cccc(Cl)c2)o1] | — | δ 11.52 (s, 1H), 8.38 (t, J = 5.9 Hz, 1H), 7.98 (s, 1H), 7.89 (t, J = 1.9 Hz, 1H), 7.80 (dt, J = 7.9, 1.4 Hz, 1H), 7.49 (t, J = 7.9 Hz, 1H), 7.40 (ddd, J = 8.1, 2.1, 1.0 Hz, 1H), 7.27 (d, J = 3.6 Hz, 1H), 7.09 (d, J = 3.6 Hz, 1H), 3.76-3.50 (m, 2H), 1.16 (t, J = 7.1 Hz, 3H). |
| PKUMDL-WL-2205 | 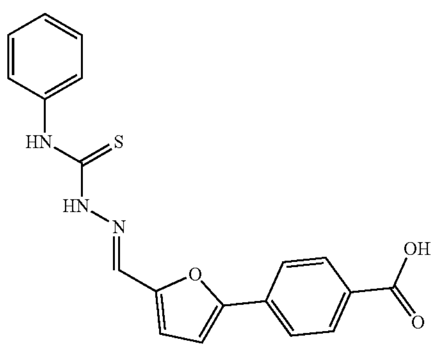 [SMILES: O=C(O)c1ccc(-c2ccc(/C=N/NC(=S)Nc3ccccc3)o2)cc1] | >300 | δ13.06 (s, 1H), 11.96 (s, 1H), 9.98 (s, 1H), 8.11 (s, 1H), 7.98 (q, J = 8.2 Hz, 4H), 7.58 (d, J = 7.8 Hz, 2H), 7.44-7.29 (m, 3H), 7.29-7.13 (m, 2H). |
| PKUMDL-WL-2206 | 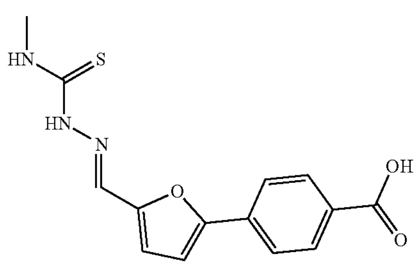 [SMILES: CNC(=S)N/N=C/c1ccc(-c2ccc(C(=O)O)cc2)o1] | 292-294 | δ 13.06 (s, 1H), 11.61 (s, 1H), 8.35 (q, J = 4.5 Hz, 1H), 8.03-7.97 (m, 3H), 7.94 (d, J = 8.3 Hz, 2H), 7.31 (d, J = 3.7 Hz, 1H), 7.10 (d, J = 3.6 Hz, 1H), 3.04 (d, J = 4.5 Hz, 3H). |
| PKUMDL-WL-2207 | 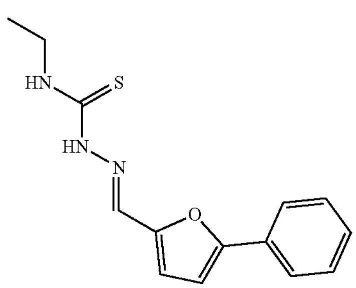 [SMILES: CCNC(=S)N/N=C/c1ccc(-c2ccccc2)o1] | 165-167 | δ 11.49 (s, 1H), 8.33 (t, J = 6.1 Hz, 1H), 7.99 (s, 1H), 7.85-7.80 (m, 2H), 7.46 (t, J = 7.6 Hz, 2H), 7.35 (t, J = 7.4 Hz, 1H), 7.14 (d, J = 3.6 Hz, 1H), 7.07 (d, J = 3.6 Hz, 1H), 3.61 (m, J = 7.0 Hz, 2H), 1.16 (t, J = 7.1 Hz, 3H). |

TABLE 2-continued

Characterization of novel furan compounds

| Number | Structure | Mp (° C.) | $^1$H NMR ($\delta$) |
|---|---|---|---|
| PKUMDL-WL-2208 | 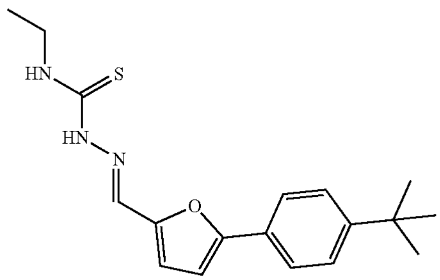 [SMILES: CCNC(=S)N/N=C/c1ccc(-c2ccc(C(C)(C)C)cc2)o1] | 142-144 | δ 11.50 (s, 1H), 8.32 (t, J = 5.9 Hz, 1H), 7.99 (s, 1H), 7.78 (s, 1H), 7.65 (m, J = 4.4, 1.7 Hz, 1H), 7.43-7.34 (m, 2H), 7.17 (d, J = 3.6 Hz, 1H), 7.08 (d, J = 3.6 Hz, 1H), 3.65-3.52 (m, 2H), 1.33 (s, 9H), 1.16 (t, J = 7.1 Hz, 3H). |
| PKUMDL-WL-2209 | 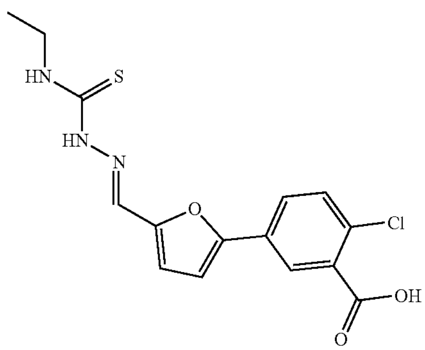 [SMILES: CCNC(=S)N/N=C/c1ccc(-c2ccc(Cl)c(C(=O)O)c2)o1] | — | δ 13.60 (s, 1H), 11.52 (s, 1H), 8.36 (t, J = 5.9 Hz, 1H), 8.14 (d, J = 2.2 Hz, 1H), 8.02-7.91 (m, 2H), 7.62 (d, J = 8.5 Hz, 1H), 7.29 (d, J = 3.6 Hz, 1H), 7.10 (d, J = 3.6 Hz, 1H), 3.66-3.54 (m, 2H), 1.16 (t, J = 7.1 Hz, 3H). |
| PKUMDL-WL-2210 | 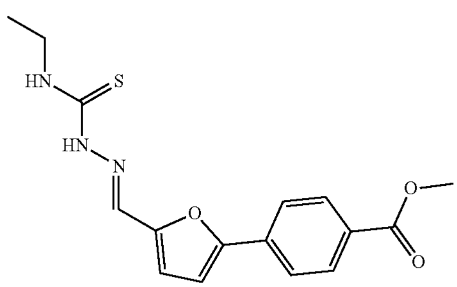 [SMILES: CCNC(=S)N/N=C/c1ccc(-c2ccc(C(=O)OC)cc2)o1] | 205-207 | δ 10.45 (s, 1H), 8.01 (d, J = 8.5 Hz, 2H), 7.93 (d, J = 8.5 Hz, 2H), 7.80 (s, 1H), 7.29 (d, J = 3.6 Hz, 1H), 6.98 (d, J = 3.6 Hz, 1H), 6.86 (t, J = 6.0 Hz, 1H), 3.87 (s, 3H), 3.25-3.12 (m, 2H), 1.10 (t, J = 7.1 Hz, 3H). |
| PKUMDL-WL-2211 | 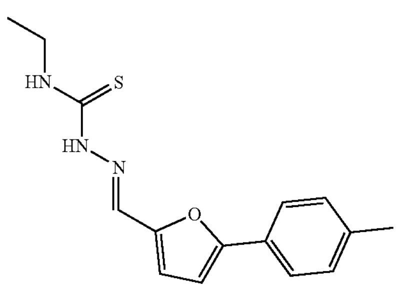 [SMILES: CCNC(=S)N/N=C/c1ccc(-c2ccc(C)cc2)o1] | 185-187 | δ 11.46 (s, 1H), 8.30 (t, J = 6.0 Hz, 1H), 7.97 (s, 1H), 7.72 (d, J = 8.2 Hz, 2H), 7.27 (d, J = 8.0 Hz, 2H), 7.05 (q, J = 3.6 Hz, 2H), 3.69-3.52 (m, 2H), 2.34 (s, 3H), 1.16 (t, J = 7.1 Hz, 3H). |

TABLE 2-continued

Characterization of novel furan compounds

| Number | Structure | Mp (° C.) | ¹H NMR (δ) |
|---|---|---|---|
| PKUMDL-WL-2212 | 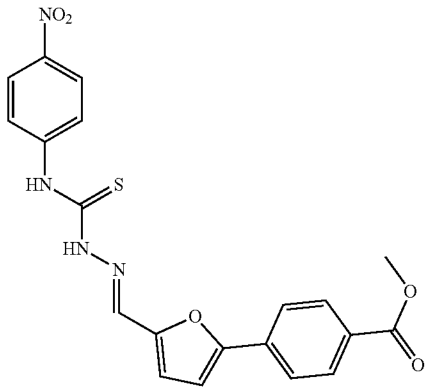 [SMILES: COC(=O)c1ccc(-c2ccc(/C=N/NC(=S)Nc3ccc([N+](=O)[O-])cc3)o2)cc1] | 250-252 | δ 13.01 (s, 1H), 12.28 (s, 1H), 10.38 (s, 1H), 8.30-8.21 (m, 2H), 8.16 (s, 1H), 8.11-8.05 (m, 2H), 8.01 (d, J = 8.6 Hz, 2H), 7.96 (d, J = 8.5 Hz, 2H), 7.36 (d, J = 3.7 Hz, 1H), 7.29 (d, J = 3.6 Hz, 1H). |
| PKUMDL-WL-2213 | 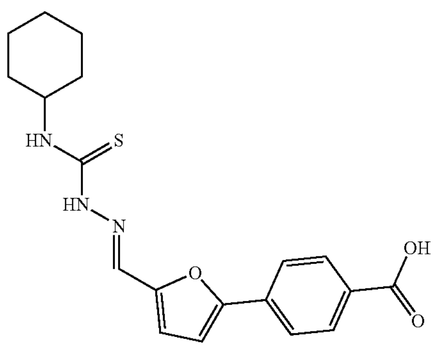 [SMILES: O=C(O)c1ccc(-c2ccc(/C=N/NC(=S)NC3CCCCC3)o2)cc1] | >300 | δ 13.02 (s, 1H), 10.44 (s, 1H), 7.99 (d, J = 8.3 Hz, 2H), 7.88 (d, J = 8.2 Hz, 2H), 7.80 (s, 1H), 7.27 (d, J = 3.6 Hz, 1H), 7.01 (d, J = 3.6 Hz, 1H), 6.43 (d, J = 8.4 Hz, 1H), 3.53 (d, J = 10.3 Hz, 1H), 1.81 (dd, J = 8.4, 4.6 Hz, 2H), 1.75-1.67 (m, 2H), 1.59 (d, J = 12.7 Hz, 1H), 1.41-1.22 (m, 4H), 1.15 (d, J = 10.3 Hz, 1H). |
| PKUMDL-WL-2214 | 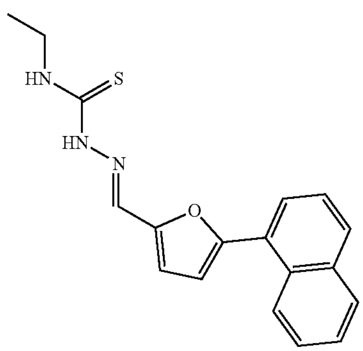 [SMILES: CCNC(=S)N/N=C/c1ccc(-c2cccc3ccccc23)o1] | — | δ 11.52 (s, 1H), 8.41 (d, J = 8.1 Hz, 1H), 8.27 (t, J = 5.8 Hz, 1H), 8.07 (s, 1H), 8.02 (m, J = 10.5, 8.1 Hz, 2H), 7.89 (dd, J = 7.3, 1.2 Hz, 1H), 7.62 (m, J = 10.4, 5.5, 5.1, 2.2 Hz, 3H), 7.20 (d, J = 3.6 Hz, 1H), 7.12 (d, J = 3.6 Hz, 1H), 3.67-3.54 (m, 2H), 1.15 (t, J = 7.1 Hz, 3H). |
| PKUMDL-WL-2215 | 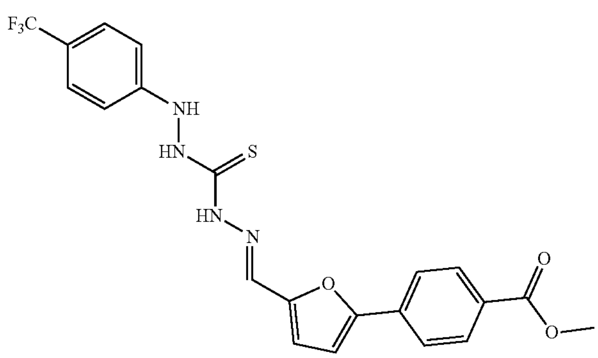 [SMILES: COC(=O)c1ccc(-c2ccc(/C=N/NC(=S)NNc3ccc(C(F)(F)F)cc3)o2)cc1] | 217-219 | δ 10.93 (s, 1H), 8.03 (d, J = 8.2 Hz, 2H), 7.94-7.85 (m, 3H), 7.57 (d, J = 8.5 Hz, 2H), 7.30 (d, J = 3.6 Hz, 1H), 7.19 (d, J = 8.4 Hz, 2H), 6.93 (d, J = 3.7 Hz, 1H), 3.87 (s, 3H). |

TABLE 2-continued

Characterization of novel furan compounds

| Number | Structure | Mp (° C.) | ¹H NMR (δ) |
|---|---|---|---|
| PKUMDL-WL-2216 | 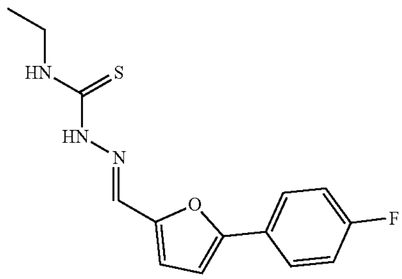 [SMILES: CCNC(=S)N/N=C/c1ccc(-c2ccc(F)cc2)o1] | 165-167 | δ 11.48 (s, 1H), 8.32 (t, J = 5.9 Hz, 1H), 7.98 (s, 1H), 7.94-7.83 (m, 2H), 7.31 (t, J = 8.9 Hz, 2H), 7.11 (d, J = 3.6 Hz, 1H), 7.06 (d, J = 3.6 Hz, 1H), 3.67-3.55 (m, 2H), 1.16 (t, J = 7.1 Hz, 3H). |
| PKUMDL-WL-2217 | 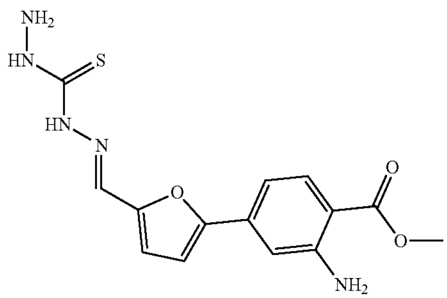 [SMILES: COC(=O)c1ccc(-c2ccc(/C=N/NC(=S)NN)o2)cc1N] | 194-196 | δ 11.57 (s, 1H), 9.53 (s, 1H), 7.95 (s, 1H), 7.78-7.72 (m, 1H), 7.20 (s, 1H), 7.17-7.09 (m, 1H), 7.07-6.92 (m, 2H), 6.77 (s, 2H), 4.97 (s, 2H), 3.79 (s, 3H). |
| PKUMDL-WL-2218 | 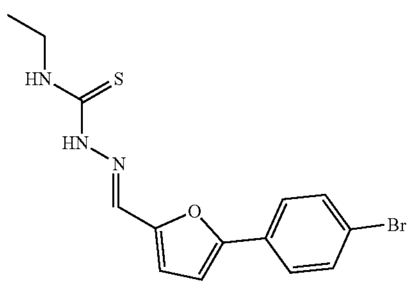 [SMILES: CCNC(=S)N/N=C/c1ccc(-c2ccc(Br)cc2)o1] | 175-177 | δ 11.50 (s, 1H), 8.34 (t, J = 5.9 Hz, 1H), 7.98 (s, 1H), 7.78 (d, J = 8.7 Hz, 2H), 7.65 (d, J = 8.7 Hz, 2H), 7.20 (d, J = 3.6 Hz, 1H), 7.07 (d, J = 3.6 Hz, 1H), 3.66-3.55 (m, 2H), 1.16 (t, J = 7.1 Hz, 3H). |
| PKUMDL-WL-2219 | 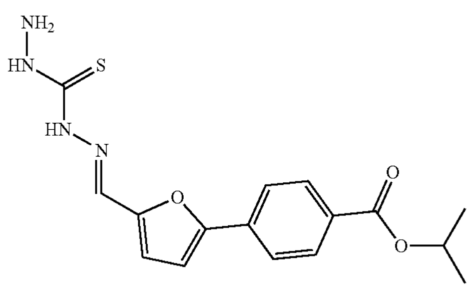 [SMILES: CC(C)OC(=O)c1ccc(-c2ccc(/C=N/NC(=S)NN)o2)cc1] | 210-212 | δ 11.57 (s, 1H), 9.66 (s, 1H), 7.98 (q, J = 7.2, 5.8 Hz, 5H), 7.30 (d, J = 3.6 Hz, 1H), 7.15 (d, J = 3.7 Hz, 1H), 5.15 (p, J = 6.2 Hz, 1H), 4.89 (s, 2H), 1.34 (d, J = 6.2 Hz, 6H). |
| PKUMDL-WL-2220 | 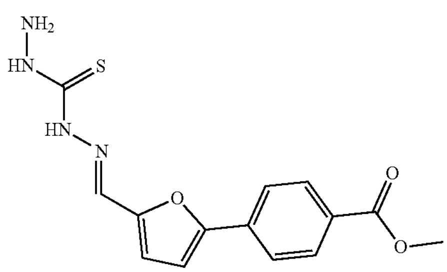 [SMILES: COC(=O)c1ccc(-c2ccc(/C=N/NC(=S)NN)o2)cc1] | 179-181 | δ 11.56 (s, 1H), 9.67 (s, 1H), 8.07-7.91 (m, 5H), 7.31 (d, J = 3.6 Hz, 1H), 7.14 (d, J = 3.7 Hz, 1H), 3.87 (s, 3H). |

TABLE 2-continued

Characterization of novel furan compounds

| Number | Structure | Mp (° C.) | ¹H NMR (δ) |
|---|---|---|---|
| PKUMDL-WL-2221 | 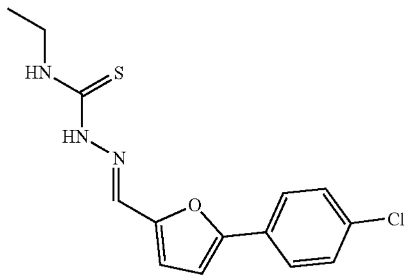 [SMILES: CCNC(=S)N/N=C/c1ccc(-c2ccc(Cl)cc2)o1] | 186-188 | δ 11.50 (s, 1H), 8.34 (t, J = 6.0 Hz, 1H), 7.98 (s, 1H), 7.85 (d, J = 8.7 Hz, 2H), 7.52 (d, J = 8.7 Hz, 2H), 7.19 (d, J = 3.6 Hz, 1H), 7.07 (d, J = 3.6 Hz, 1H), 3.69-3.52 (m, 2H), 1.16 (t, J = 7.1 Hz, 3H). |
| PKUMDL-WL-2222 | 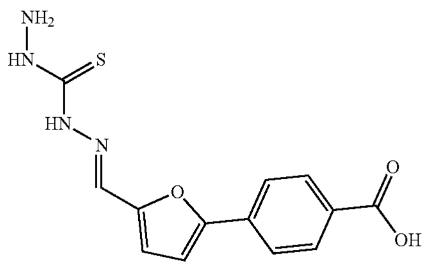 [SMILES: NNC(=S)N/N=C/c1ccc(-c2ccc(C(=O)O)cc2)o1] | 220-222 | δ 11.55 (s, 1H), 9.66 (s, 1H), 8.05-7.88 (m, 5H), 7.29 (d, J = 3.6 Hz, 1H), 7.13 (d, J = 3.6 Hz, 1H). |
| PKUMDL-WL-2223 | 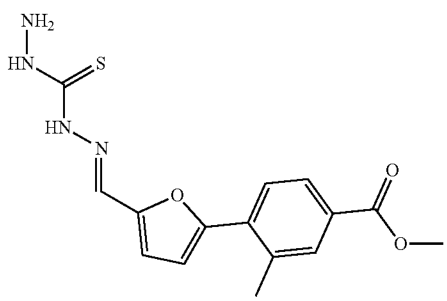 [SMILES: COC(=O)c1ccc(-c2ccc(/C=N/NC(=S)NN)o2)c(C)c1] | 211-213 | δ 11.50 (s, 1H), 9.49 (s, 1H), 8.20 (s, 1H), 7.93 (s, 1H), 7.84 (d, J = 8.3 Hz, 1H), 7.61 (d, J = 8.2 Hz, 1H), 7.50 (d, J = 3.9 Hz, 1H), 7.34 (d, J = 3.8 Hz, 1H), 4.87 (s, 2H), 3.87 (s, 3H). |
| PKUMDL-WL-2224 | 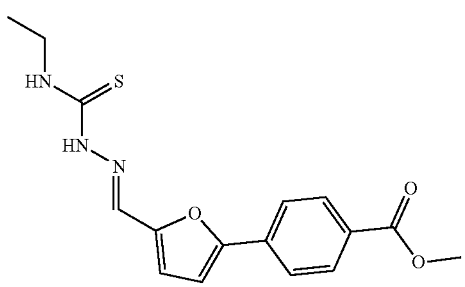 [SMILES: CCNC(=S)N/N=C/c1ccc(-c2ccc(C(=O)OC)cc2)o1] | 205-207 | δ 11.54 (s, 1H), 8.36 (t, J = 6.0 Hz, 1H), 8.02 (d, J = 8.7 Hz, 2H), 7.96 (d, J = 8.5 Hz, 2H), 7.33 (d, J = 3.6 Hz, 1H), 7.13 (d, J = 3.7 Hz, 1H), 3.87 (s, 3H), 3.67-3.55 (m, 2H), 1.17 (t, J = 7.1 Hz, 3H). |
| PKUMDL-WL-2225 | 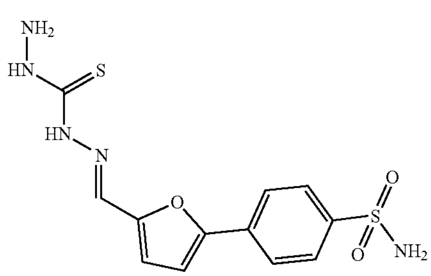 [SMILES: NNC(=S)N/N=C/c1ccc(-c2ccc(S(N)(=O)=O)cc2)o1] | 182-184 | δ 11.56 (s, 1H), 9.67 (s, 1H), 8.02 (d, J = 8.2 Hz, 2H), 7.95 (s, 1H), 7.90-7.82 (m, 2H), 7.41 (s, 2H), 7.29 (d, J = 3.6 Hz, 1H), 7.14 (d, J = 3.6 Hz, 1H), 4.90 (s, 2H). |

TABLE 2-continued

Characterization of novel furan compounds

| Number | Structure | Mp (° C.) | $^1$H NMR (δ) |
|---|---|---|---|
| PKUMDL-WL-2226 | 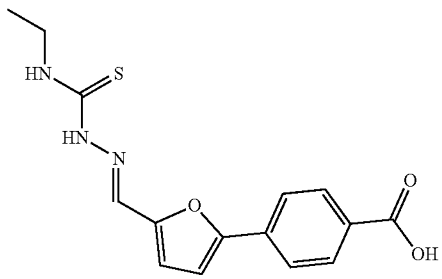 [SMILES: CCNC(=S)N/N=C/c1ccc(-c2ccc(C(=O)O)cc2)o1] | 262-264 | δ 11.55 (s, 1H), 8.38 (t, J = 5.9 Hz, 1H), 8.04-7.97 (m, 3H), 7.93 (d, J = 8.4 Hz, 2H), 7.31 (d, J = 3.6 Hz, 1H), 7.12 (d, J = 3.6 Hz, 1H), 3.61 (p, J = 7.0 Hz, 2H), 1.17 (t, J = 7.1 Hz, 3H). |
| PKUMDL-WL-2227 | 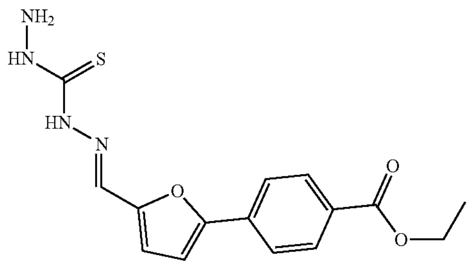 [SMILES: CCOC(=O)c1ccc(-c2ccc(/C=N/NC(=S)NN)o2)cc1] | 195-197 | δ 11.56 (s, 1H), 9.67 (s, 1H), 7.99 (q, J = 9.7, 9.1 Hz, 5H), 7.31 (d, J = 3.7 Hz, 1H), 7.15 (d, J = 3.7 Hz, 1H), 4.89 (s, 2H), 4.33 (q, J = 7.0 Hz, 2H), 1.34 (t, J = 7.1 Hz, 3H). |
| PKUMDL-WL-2228 | 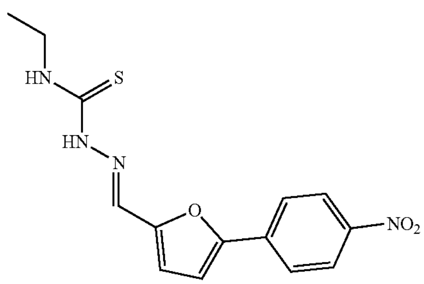 [SMILES: CCNC(=S)N/N=C/c1ccc(-c2ccc([N+](=O)[O-])cc2)o1] | 172-174 | δ 11.60 (s, 1H), 8.45-8.37 (m, 1H), 8.30 (d, J = 8.6 Hz, 2H), 8.07 (d, J = 8.6 Hz, 2H), 8.02 (s, 1H), 7.48 (d, J = 3.7 Hz, 1H), 7.17 (d, J = 3.7 Hz, 1H), 3.62 (m, 2H), 1.17 (t, J = 7.1 Hz, 3H). |
| PKUMDL-WL-2229 | 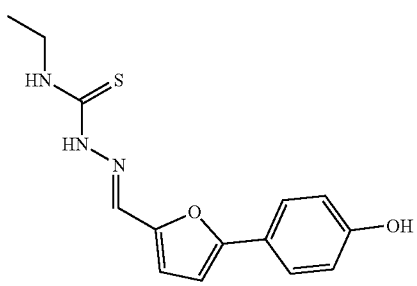 [SMILES: CCNC(=S)N/N=C/c1ccc(-c2ccc(O)cc2)o1] | — | δ 11.42 (s, 1H), 9.79 (s, 1H), 7.95 (s, 1H), 7.65 (d, J = 8.6 Hz, 2H), 7.00 (d, J = 3.6 Hz, 1H), 6.88 (d, J = 3.6 Hz, 1H), 6.84 (d, J = 8.6 Hz, 2H), 3.63-3.56 (m, 3H), 1.16 (t, J = 7.1 Hz, 3H). |
| PKUMDL-WL-2230 | 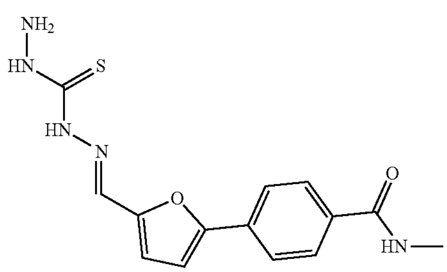 [SMILES: CNC(=O)c1ccc(-c2ccc(/C=N/NC(=S)NN)o2)cc1] | 224-226 | δ 11.53 (s, 1H), 9.66 (s, 1H), 8.49 (d, J = 4.8 Hz, 1H), 7.97-7.80 (m, 5H), 7.24 (d, J = 3.6 Hz, 1H), 7.12 (d, J = 3.6 Hz, 1H), 4.89 (s, 2H), 3.57 (s, 1H), 2.80 (d, J = 4.5 Hz, 3H). |

TABLE 2-continued

Characterization of novel furan compounds

| Number | Structure | Mp (° C.) | $^1$H NMR (δ) |
|---|---|---|---|
| PKUMDL-WL-2231 | 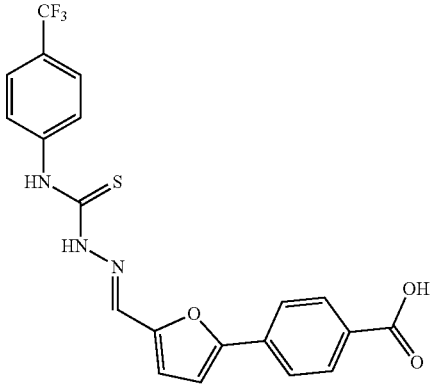 [SMILES: O=C(O)c1ccc(-c2ccc(/C=N/NC(=S)Nc3ccc(C(F)(F)F)cc3)o2)cc1] | 217-219 | δ 12.14 (s, 1H), 10.21 (s, 1H), 8.63 (s, 1H), 8.14 (s, 1H), 8.01 m, 3H), 7.94-7.88 (m, 3H), 7.75 (t, J = 7.1 Hz, 1H), 7.36 (d, J = 3.7 Hz, 1H), 7.32-7.24 (m, 2H).z |

Implementation Example 4. Determination of In Vitro Enzymatic Activity of PHGDH Compounds by Fluorescence Kinetic Method The activity of recombinant PHGDH was measured by monitoring the reduced nicotinamideadenine dinucleotide (NADH) to nicotinamideadenine dinucleotide (NAD$^+$) change in fluorescence emission at 456 nm. PHGDH (final concentration of 30 ng/μL) was first pre-incubated with enzyme samples in the assay buffer (25 mM HEPES, pH 7.1, 400 mM KCl, 5 μM phosphopyridoxa (PLP), 0.5 mM α-ketoglutarate, 150 μM NADH, PSAT1) for 10 min in 96-well plate, then 10 μL of DMSO (control) or a small molecule of DMSO solution was added, shaken at 550 rpm for 5 minutes at 25° C. and balanced for 5 minutes. In the in vivo testing system of enzyme, each compound was dissolved in DMSO at a final concentration of 5% (v/v), which did not affect the assay signal. The reaction was started by adding L-phospho-O-serine (Pser) solution. The UV-visible microplate reader was used to monitor the change of NADH consumption at 456 nm with time. Protein activity was assessed by using an initial rate of reaction within 30 s, at which time NADH consumption was linear over time. The enzymatic inhibition ability of sixty-three compounds was first measured at 50 μM, compounds with percentage inhibition of PHGDH larger than 50% were selected for further studies, and IC$_{50}$ values were obtained (Table 3).

TABLE 3

IC$_{50}$ values of the compounds

| Compounds | IC$_{50}$ (μM) |
|---|---|
| PKUMDL-WL-2101 | 34.8 ± 3.6 |
| PKUMDL-WL-2128 | 36.1 ± 4.2 |
| PKUMDL-WL-2201 | 35.7 ± 8.6 |
| PKUMDL-WL-2212 | 29.8 ± 9.4 |
| PKUMDL-WL-2220 | 8.9 ± 1.8 |
| PKUMDL-WL-2222 | 16.7 ± 1.6 |
| PKUMDL-WL-2225 | 38.9 ± 1.2 |
| PKUMDL-WL-2226 | 35.5 ± 1.1 |
| PKUMDL-WL-2228 | 37.0 ± 2.8 |
| PKUMDL-WL-2229 | 30.3 ± 4.5 |

Implementation Example 5. Inhibitory Activities of the Compounds on Cancer Cells The biological activities of the compounds at the cellular level were investigated. A series of cancer cells and normal mammary epithelial cells were selected, and the experimental method of MTT (3-(4,5)-dimethylthiahiazo (-z-y 1)-3,5-di-phenytetrazoliumromide) was used.

The specific method: firstly, PHGDH-sensitive breast cancer cells MDA-MB-468 (5,000 cells/well) and HCC70 (5,000 cells/well), PHGDH-insensitive breast cancer cells MCF-7 (3,000 cells/well), MDA-MB-231 (2,000 cells/well) and ZR-75-1 (4,000 cells/well), colon cancer cell DLD-1 (2,000 cells/well) and normal breast epithelial cells MCF-10A (3,000 cells/well) in the exponential growth were plated into 96-well culture plates and treated in triplicate with or without various concentrations of activated compounds from the enzymatic bioassays. They adhered to the wall over night. The compounds were added from stock solutions in DMSO and the final concentration of DMSO in the medium was 0.2%. After 72 h, 20 μL 5 mg/ml MTT was added to each well and incubated for at least 4 h. After the incubation, medium containing compounds and MTT was removed from each well and 200 μL DMSO was added, followed by shaking slowly for 10 min at 37° C. The number of viable cells was assessed by spectrophotometry at 570 nm, and calculated as the percentage of absorbance of treated cells relative to that of solvent controls. Results were expressed as a percentage of viable cells and the EC$_{50}$ was calculated by using the Hill equation.

PKUMDL-WL-2101 and PKUMDL-WL-2201 exhibited micromolar inhibitory activity at the cellular level (see Table 4). PKUMDL-WL-2101 showed EC$_{50}$ values of 7.70 and 10.8 μM for PHGDH-sensitive breast cancer cells MDA-MB-468 and HCC70, respectively, and exhibited EC$_{50}$ values of 27.7, 83.4 and 139 μM for PHGDH-insensitive breast cancer cells MDA-MB-231, ZR-75-1 and MCF-7, respectively. Its EC$_{50}$ value for colon cancer cells was 18.3 μM. Meanwhile, PKUMDL-WL-2101 exerted weak cytotoxic effects on the MCF-10A cell line with a EC$_{50}$ of 45.8 μM. As for PKUMDL-WL-2201, the EC$_{50}$ values were 6.90 and 10.0 μM in MDA-MB-468 and HCC70 cell lines sensitive to PHGDH, respectively and the EC$_{50}$ values were >200, 125 and >200 μM in MDA-MB-231, ZR-75-1 and MCF-7 cell lines insensitive to PHGDH, respectively. Its EC$_{50}$ in colon cancer cell line was 167 μM. Similarly, PKUMDL-WQ-2201 exerted weak cytotoxic effects on the MCF-10A cell line with an $EC_{50}$ of 64.7 μM.

TABLE 4

Lethal activities of PKUMDL-WL-2101 and PKUMDL-WL-2201 in cancer cells

| Compounds | DLD-1 | MDA-MB-468 | HCC70 | MDA-MB-231 | ZR-75-1 | MCF-7 | MCF-10A |
|---|---|---|---|---|---|---|---|
| PKUMDL-WL-2101 | 18.3 ± 1.4 | 7.7 ± 0.1 | 10.8 ± 2.0 | 27.7 ± 3.8 | 83.4 ± 5.6 | 139 ± 6 | 45.8 ± 2.3 |
| PKUMDL-WQ-2201 | 167 ± 14 | 6.9 ± 1.4 | 10.0 ± 1.8 | >200 | 125 ± 8 | >200 | 64.7 ± 4.5 |

Figure 3:
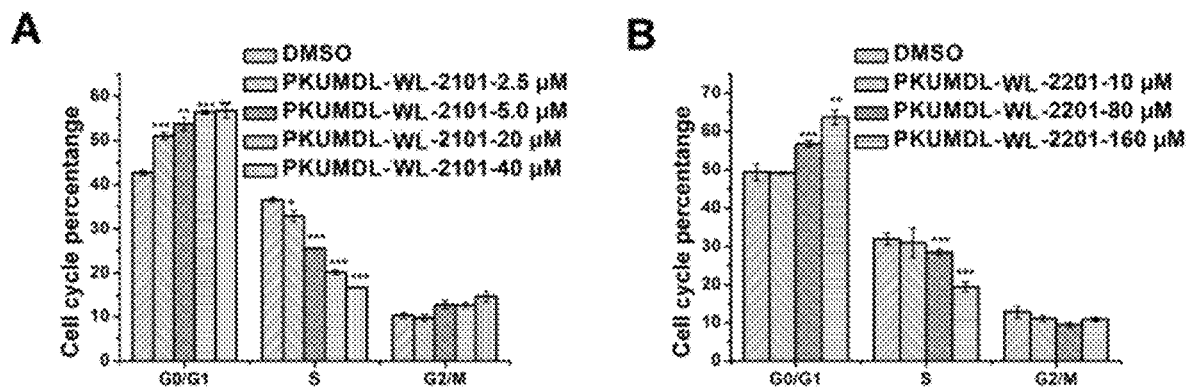
FIG. 3 depicts effects of PKUMDL-WL-2101 (A) and PKUMDL-WL-2201 (B) on mitotic cycle of breast cancers in Implementation Example 5.

MDA-MB-468 Cells (300,000 cells/well) in exponential growth were plated into 6-well culture plates and then treated in triplicate with or without various concentrations of PKUMDL-WL-2101. After 24 h, cells were harvested by trypsinization and centrifuged, and then fixed in 70% ice-cold ethanol, washed twice with 1×PBS, and kept at 4° C. overnight. The fixed cells were afterwards washed in 1×PBS and resuspended in 1×PBS containing 0.5% triton-x-100, 50 μg/ml Prodiumiodide (PI) and 50 μg/ml DNase-free RNase. The cell suspension was incubated in the dark for 30 min at 37° C. and analyzed by using a BD FACSCanto™ cytometer. PKUMDL-WL-2101 and PKUMDL-WL-2201 arrested the cell cycle at the $G_0/G_1$-phase in a dose-dependent manner (FIG. 3). These two compounds led to a significantly higher percentage of $G_0/G_1$-phase cells and lower frequency of S-phase cells. These results demonstrated that PKUMDL-WL-2101 and PKUMDL-WL-2201 showed good lethal activity of cells for PHGDH-sensitive breast cancer cells.

Implementation Example 6. Bioactivity Effects of Compounds in Mouse Xenograft Models 1. PKUMDL-WL-2101 or PKUMDL-WL-2201 injected separately All animal experiments were performed in compliance with guidelines of the Animal Welfare Act and the guide for the care and use of laboratory animals following protocols approved by the Institutional Animals Care and Use Committee (IACUC). Firstly, MDA-MB-468 cells were injected into the fourth mammary fat pad of NOD.CB17 Scid/J mice at $2×10^5$ cells per injection site. When the average tumor volume reached 30 mm³, the mice were randomized into 3 groups (n=5): vehicle control (10% DMSO, 20% EL and 70% PBS, IP), 20 mg/kg/day PKUMDL-WL-2101 or PKUMDL-WL-2201 (IP). The tumor volumes were measured every two days and calculated by using the following formula width² (mm)×length (mm)×0.5.

Figure 4:
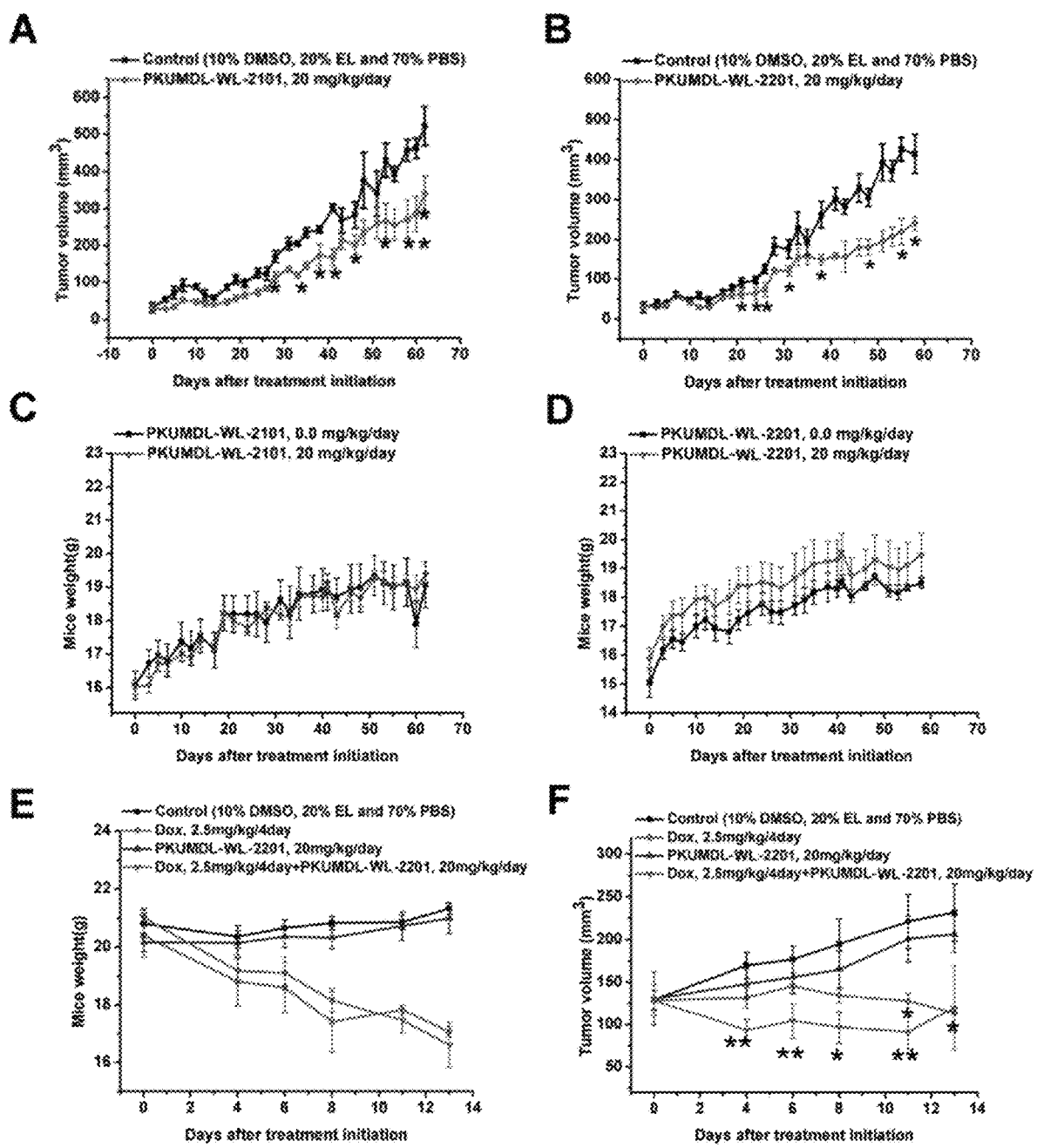
FIG. 4 depicts biologic activities of compounds PKUMDL-WL-2101 (A, C) and PKUMDL-WL-2201 (B, D, E, F) in mouse xenograft model in Implementation Example 6.

As depicted in FIG. 4, PKUMDL-WL-2101 or PKUMDL-WL-2201 exhibited substantial inhibitory effects on MDA-MB-468 xenografts compared with vehicle-treated mice after 30 days of drug delivery (FIGS. 4A and 4B). The compounds appeared to be tolerated as all mice were able to maintain normal body weight over the course of the experiments (FIGS. 4C and 4D). The experimental results are statistically significant, and the P value is less than 0.05.
2. The Combination Treatment of PKUMDL-WL-2201 with Doxorubicin.

As described above, MDA-MB-468 cells were injected into the fourth mammary fat pad of NOD.CB17 Scid/J mice at $2×10^5$ cells per injection site. When the average tumor volume reached 150 mm³, the mice were randomized into 5 groups (n=5): vehicle group (10% DMSO, 20% EL and 70% PBS), 2.5 mg/kg/4 day doxorubicin, 20 mg/kg/day PKUMDL-WL-2201 and 20 mg/kg/day PKUMDL-WL-2201+2.5 mg/kg/4 day doxorubicin. Tumor volume growth curves and survival curves of mouse were monitored every two days, tumor sizes were measured by calipers, and tumor volumes were calculated as described above.

Because of the toxicity of doxorubicin, mice treated with doxorubicin began to die after 13 days of drug delivery. Therefore, all the combination experiments were ended at the time point of 11 days. As shown in FIGS. 4E and 4F, the combination of PKUMDL-WL-2201 and doxorubicin exhibited significant inhibitory effects on xenografts compared with agent alone or vehicle control group, and was significantly different from the tumor growth inhibition effect of agent alone. The best efficacy of combination therapy occurred in the sixth day of drug delivery, with the percentage inhibition of tumor growth for 41%.

In all, the compounds in the present invention can selectively inhibit PHGDH activity in enzymatic activity assays, cell-based assays and mouse tumor model.

What is claimed is:
1. A chemical compound having structural formula (II)

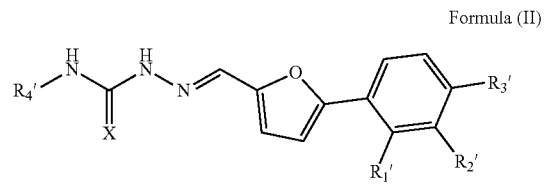

Formula (II)

or a salt or a solvate thereof, wherein $R_1'$ and $R_3'$ are identical or different, wherein each of $R_1'$ and $R_3'$ independently represents hydrogen, hydroxyl, amino, carboxyl, alkyl, alkoxy, haloalkyl, carboxylic ester, sulfonamide, amide or N-alkyl substituted amide, wherein $R_2'$ is hydrogen, hydroxyl, amino, carboxyl, alkyl, alkoxy, haloalkyl, carboxylic ester, sulfonamide, amide or N-alkyl substituted amide, or wherein two adjacent substituents (R1' and R2' or R2' and R3') form part of a ring, wherein $R_4'$ is alkyl, haloalkyl, amino, cycloalkyl, substituted or unsubstituted aryl, wherein X is nitrogen or sulfur.

2. A chemical compound according to claim 1, wherein when one or more of $R_1'$, $R_2'$ and $R_3'$ are one or more alkyl groups, the one or more alkyl groups are C1~C12 alkyl groups, wherein when one or more of $R_1'$, $R_2'$ and $R_3'$ are one or more alkoxy groups, the one or more alkoxy groups are C1~C8 alkoxy groups, wherein when one or more of $R_1'$, $R_2'$ and $R_3'$ are one or more haloalkyl groups, the one or more haloalkyl groups are C1~C12 alkyl groups substituted by one or more halo, wherein when one or more of $R_1'$, $R_2'$ and $R_3'$ are one or more carboxylic ester groups, the one or more carboxylic ester groups are C1~C8 ester group, wherein when one or more of $R_1'$, $R_2'$ and $R_3'$ are one or more N-alkyl substituted amide groups, the one or more N-alkyl substituted amide groups are C1~C12 alkyl substituted amide group.

3. A chemical compound according to claim 1, wherein when $R_1'$ and $R_2'$ or $R_2'$ and $R_3'$ are linked into ring, the two adjacent substituents represent buta-1,3-diene-1,4-diyl or buta-2-ene-1,4-dily.

4. A chemical compound according to claim 1, wherein when $R_4'$ is an alkyl group, the alkyl group is a C1~C12 alkyl group, wherein when $R_4'$ is a haloalkyl group, the haloalkyl group is a C1~C12 alkyl group substituted by one or more halo, wherein when $R_4'$ is a cycloalkyl group, the cycloalkyl group is a C5~C7 membered cycloalkyl group.

5. A chemical compound according to claim 1, wherein when $R_4'$ is unsubstituted or substituted aryl, the aryl is phenyl, wherein the substituted aryl is 4-substituted phenyl.

6. A chemical compound according to claim 5, wherein the substituent group on 4- of the 4-substituted phenyl is C1~C6 alkyl, C1~C6 alkyl group substituted by one or more halo, nitro, or C1~C4 alkoxy.

7. A chemical compound according to claim 1, wherein the compound having structural Formula (II) is one of the following compounds (PKUMDL-WL-2201 to PKUMDL-WL-2231):

PKUMDL-WL-2201

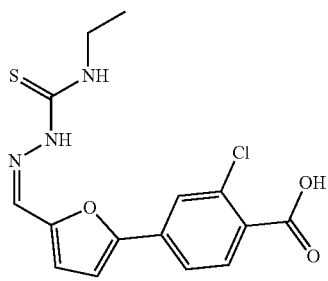

PKUMDL-WL-2202

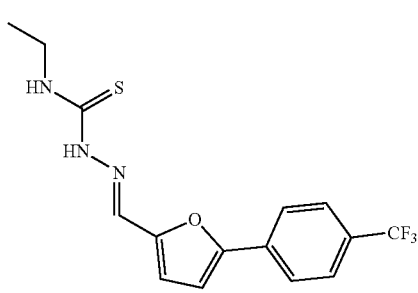

PKUMDL-WL-2203

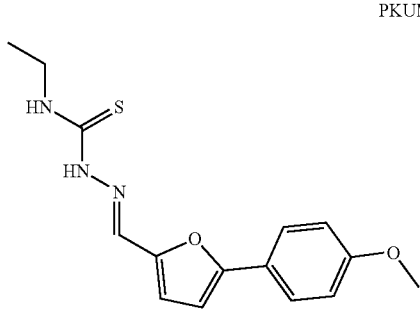

PKUMDL-WL-2205

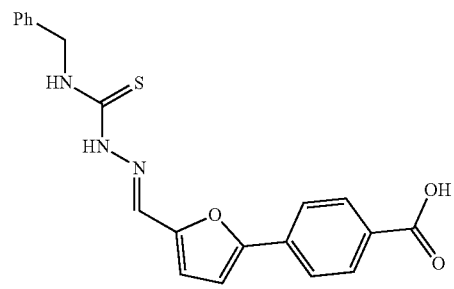

PKUMDL-WL-2206

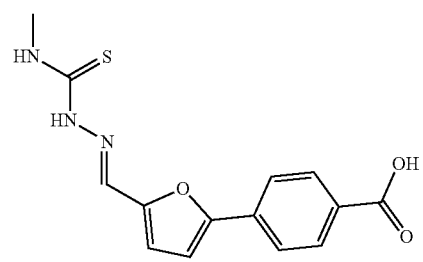

PKUMDL-WL-2207

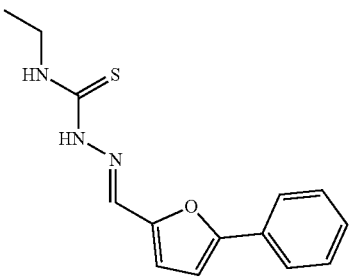

PKUMDL-WL-2208

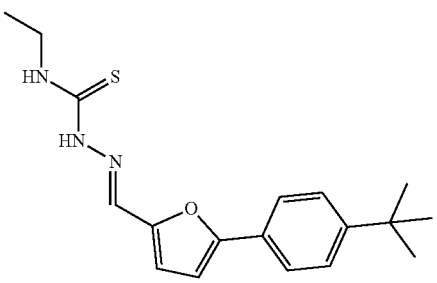

PKUMDL-WL-2210

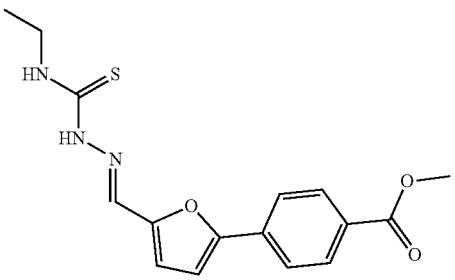

PKUMDL-WL-2211
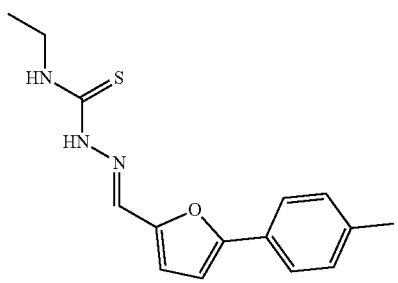
PKUMDL-WL-2212
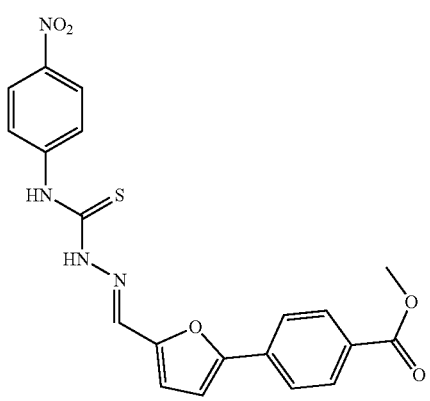
PKUMDL-WL-2213
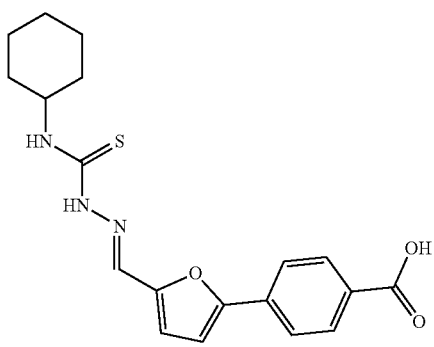
PKUMDL-WL-2214
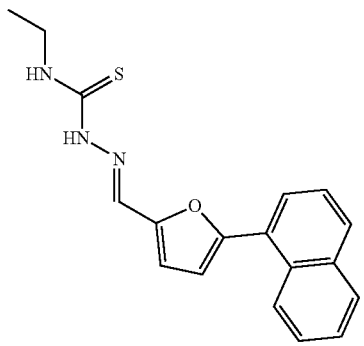
PKUMDL-WL-2215
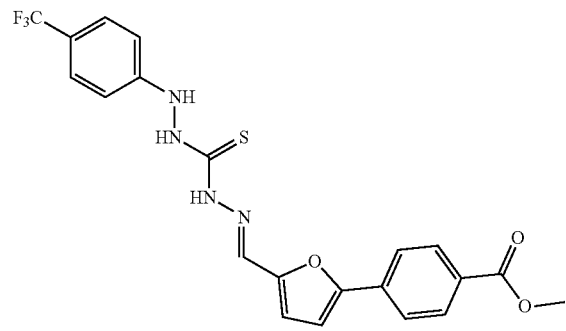
PKUMDL-WL-2216
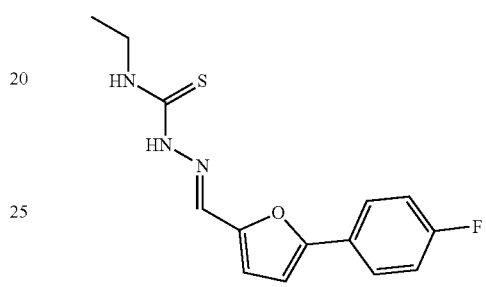
PKUMDL-WL-2217
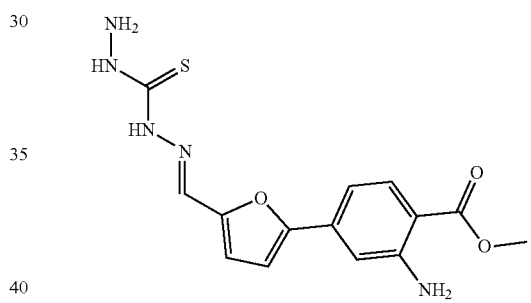
PKUMDL-WL-2219
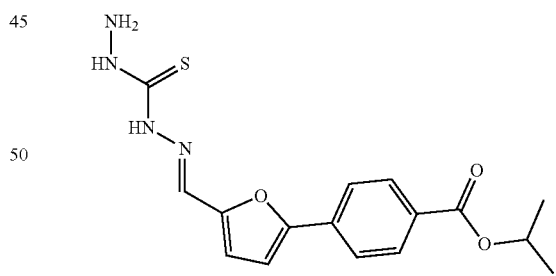
PKUMDL-WL-2220
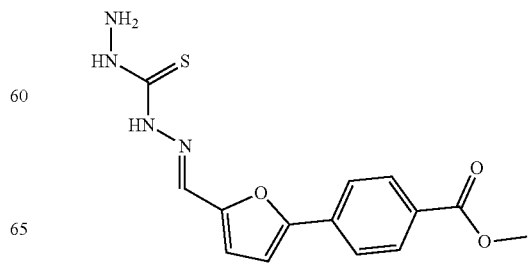

PKUMDL-WL-2222
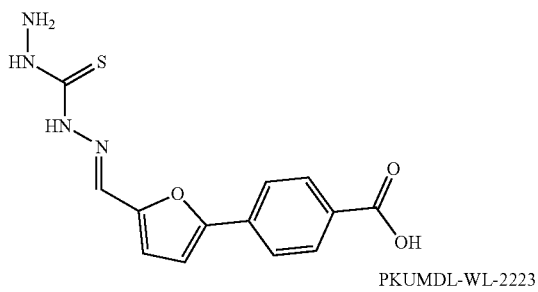
PKUMDL-WL-2223
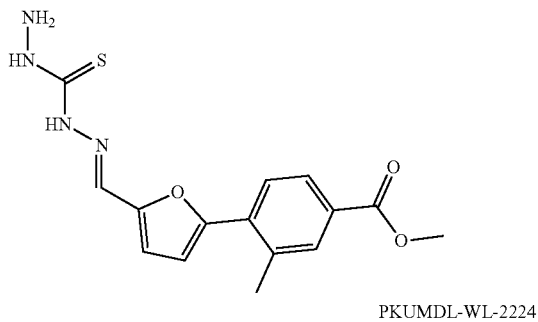
PKUMDL-WL-2224
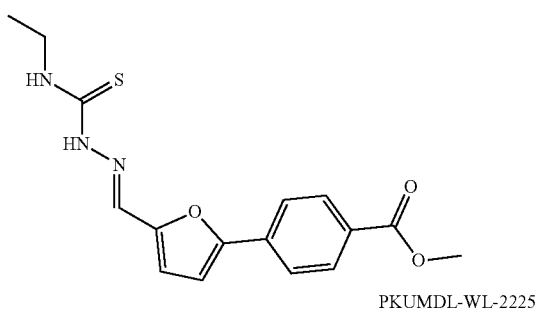
PKUMDL-WL-2225
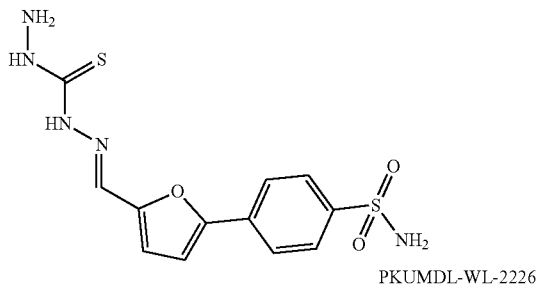
PKUMDL-WL-2226
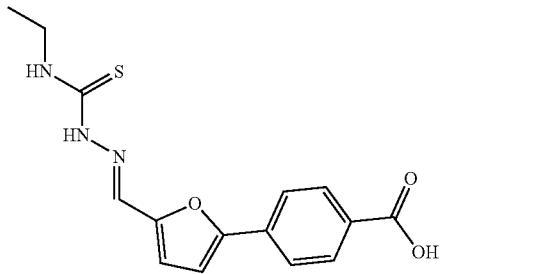
PKUMDL-WL-2227
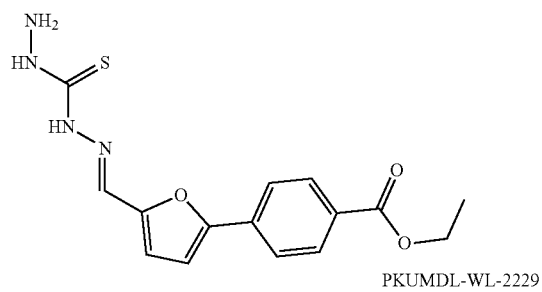
PKUMDL-WL-2229
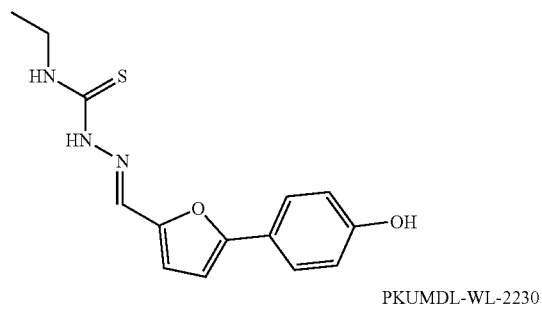
PKUMDL-WL-2230
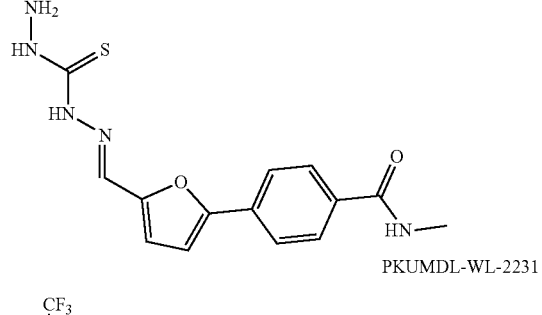
PKUMDL-WL-2231
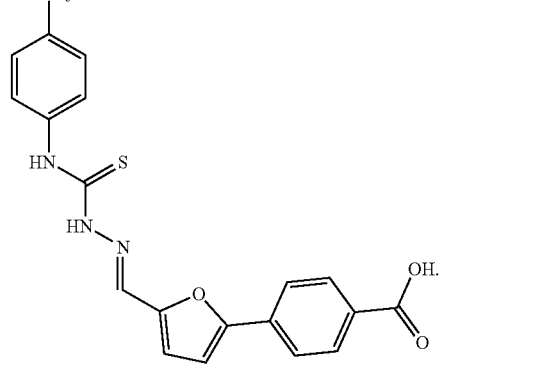
8. A pharmaceutical composition for preparing PHGDH inhibitors comprising a compound having structural Formula (II) according to claim 1, or a pharmaceutical salt thereof.
* * * * *